United States Patent
Babin et al.

(10) Patent No.: US 6,946,460 B2
(45) Date of Patent: Sep. 20, 2005

(54) AZOLE OR TRIAZOLE DERIVATIVES, METHOD FOR PREPARING SAME AND USE THEREOF AS FUNGICIDES

(75) Inventors: Didier Babin, Montigny (FR); John Bernard Weston, Maisons Laffitte (FR)

(73) Assignee: Aventis Pharma S.A., Antony Cedex (FR)

(*) Notice: Subject to any disclaimer, the term of this patent is extended or adjusted under 35 U.S.C. 154(b) by 68 days.

(21) Appl. No.: 10/477,112

(22) PCT Filed: May 2, 2002

(86) PCT No.: PCT/FR02/01521
§ 371 (c)(1),
(2), (4) Date: Sep. 7, 2004

(87) PCT Pub. No.: WO02/090354
PCT Pub. Date: Nov. 14, 2002

(65) Prior Publication Data
US 2005/0043540 A1 Feb. 24, 2005

(30) Foreign Application Priority Data
May 4, 2001 (FR) .............................. 01 05958

(51) Int. Cl.[7] ................... C07D 233/54; A61K 31/415; A61K 31/41

(52) U.S. Cl. .................... 514/228.8; 514/383; 514/399; 544/97; 548/267.2; 548/335.5

(58) Field of Search .............................. 514/228.8, 383, 514/399; 544/97; 548/267.2, 335.5

(56) References Cited

FOREIGN PATENT DOCUMENTS

| EP | 0050298 | 4/1982 |
|---|---|---|
| EP | 0121753 | 10/1984 |
| WO | WO 00/20413 | 4/2000 |

*Primary Examiner*—Zinna Northington Davis
(74) *Attorney, Agent, or Firm*—Balaram Gupta

(57) ABSTRACT

The invention concerns novel azole or triazole derivatives of formula (I), wherein X, $Ar^1$, $Ar^2$, $Ar^3$, A, B, and $R^1$ are as defined herein, their preparation method and their use as fungicides.

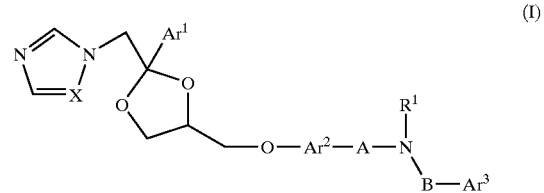

(I)

23 Claims, No Drawings

AZOLE OR TRIAZOLE DERIVATIVES, METHOD FOR PREPARING SAME AND USE THEREOF AS FUNGICIDES

The present invention relates to new azole or triazole derivatives, their preparation process and their use as fungicides.

A number of compounds having an antifungal activity are known in the prior art. Azole derivatives as defined in the following applications: EP 0 121 753 A (Hoechst AG), EP 0 050 298 A (Hoechst AG), U.S. Pat. No. 2,813,872 (J Schmutz), WO 00/20413 (Hoechst Marion Roussel) can in particular be mentioned. Moreover, the new antifungal compounds must be able to have improved solubility and must also be able to be absorbed more easily. Nevertheless, a real need exists to make use of new antifungal compounds, the present strains being able to be or become resistant to the standard agents, in particular when the latter possess only a fungistatic activity. Finally, the incidence of Candida albicans, as an infectious agent, is increasing steadily, in particular vis-à-vis immunodeficient patients, for example as a result of HIV infection, and therefore requires new treatments.

The object of the present invention is to provide new compounds having an antifungal activity, in particular vis-à-vis Candida or Aspergillus strains.

A subject of the invention is the compounds of formula (I):

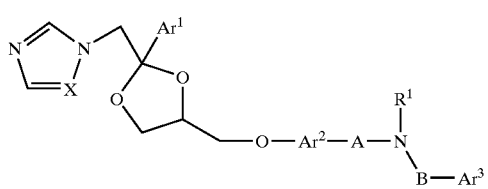

in which

X is a nitrogen atom or a CH group, $Ar^1$ represents a carbocyclic or heterocyclic aryl, non-substituted or substituted by one or more $R^2$, $R^3$ or $R^4$ radicals $Ar^2$ represents a phenylene or naphthylene, non-substituted or substituted by one or more $R^5$, $R^6$ or $R^7$ radicals $Ar^3$ represents a carbocyclic or heterocyclic aryl, non-substituted or substituted by one or more $R^8$, $R^9$ or $R^{10}$ radicals A represents a $(C_1-C_4)$-alkylene radical or a C(O) radical, B represents a $(C_1-C_4)$-alkylene-CH=CH— radical or a $(C_1-C_4)$-alkylene-cyclopropylene radical, said cyclopropylene or —CH=CH— radicals being non-substituted or substituted by an $R^2$ and/or $R^3$ radical, $R^1$ represents a hydrogen atom, an —SO$_3$H group or a $(C_1-C_6)$-alkyl radical, non-substituted or substituted by a radical as defined for $R^2$, $R^2$, $R^3$, $R^4$, $R^5$, $R^6$, $R^7$, $R^5$, $R^9$ or $R^{10}$, which are identical or different, represent fluorine, chlorine, bromine, cyano, mono- bi- or trihalogeno($C_1-C_8$)alkyl, mono- bi- or trihalogeno($C_1-C_8$)-alkyloxy, hydroxy, nitro, carboxyl, formyl, —SO$_3$H, —OSO$_3$H, $(R^{11}O)_2P(O)$—, $(R^{11}O)_2P(O)$—O—, amino, $(C_1-C_8)$-alkylamino, di(($C_1-C_8$)alkyl)amino, $(C_5-C_{14})$-aryl-$(C_1-C_6)$-alkylenamino or $(C_5-C_{14})$-arylamino, $(C_1-C_8)$-alkyl, $(C_5-C_{14})$-aryl, a heterocycle optionally substituted by oxo, $(C_5-C_{14})$-aryl-$(C_1-C_6)$alkyl, amino-$(C_1-C_6)$-alkyl, $(C_1-C_8)$-alkylamino-$(C_1-C_6)$-alkyl, di-(($C_1-C_8$)alkyl)amino-$(C_1-C_6)$-alkyl, hydroxy-$(C_1-C_6)$alkyl, $(C_1-C_6)$-alkyloxy-$(C_1-C_6)$-alkyl, $(C_1-C_8)$-alkyloxy optionally interrupted by one or more oxygen atoms, $(C_5-C_{14})$-aryl-$(C_1-C_6)$-alkylenoxy, $(C_5-C_{14})$-aryloxy, hydroxy-$(C_1-C_6)$alkylenoxy, $(C_1-C_6)$-alkyloxy-$(C_1-C_6)$alkylenoxy, amino-$(C_1-C_6)$-alkylenoxy, $(C_1-C_6)$-alkylamino-$(C_1-C_6)$-alkylenoxy, di(($C_1-C_8$)-alkyl)amino-$(C_1-C_6)$-alkylenoxy, methylenedioxy, $(C_1-C_6)$-alkyloxycarbonyl, $(C_1-C_6)$-alkylcarbonyl, $(C_5-C_{14})$aryl-$(C_1-C_6)$-alkylenecarbonyl, $(C_5-C_{14})$-aryl-carbonyl, $(C_1-C_6)$-alkylaminocarbonyl, $(C_1-C_6)$alkanoylamino, $(C_1-C_6)$-alkylsulphonylamino, $(C_1-C_{14})$-arylsulphonylamino, $(C_5-C_{14})$-aryl-$(C_1-C_6)$-alkylenesulphonylamino, $(C_1-C_6)$-alkylaminosulphonyl, $(C_5-C_{14})$-aryl-$(C_1-C_6)$-alkylenaminosulphonyl, $(C_1-C_6)$-alkyl-sulphonyl, $(C_5-C_{14})$-aryl-$(C_1-C_8)$-alkylenesulphonyl or $(C_5-C_{14})$-aryl-sulphonyl, said alkyl, aryl radicals or heterocycles being themselves non-substituted or substituted by one or more groups mentioned above.

$R^{11}$ represents hydrogen, $(C_1-C_{10})$-alkyl, $(C_6-C_{14})$-aryl or $(C_6-C_{14})$-aryl-$(C_1-C_6)$-alkyl, in all their possible stereoisomeric forms and their mixtures, as well as their physiologically acceptable addition salts and their prodrugs.

All the radicals which can be found several times in the compounds of formula (I), for example, the radical $R^2$, are independent of one another other and can be identical or different.

The alkyl radicals mentioned above can be linear, branched or cyclic, saturated or mono- or poly-unsaturated. This also applies when they carry a substituent or when they are included in groups such as for example alkoxy, alkoxycarbonyl or aralkyl.

By saturated $(C_1-C_8)$-alkyl is meant the methyl, ethyl, propyl, butyl, pentyl, hexyl, heptyl, octyl, nonyl radicals, the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Among the preferred radicals, methyl, ethyl, n-propyl, isopropyl, n-butyl, isobutyl, and tert-butyl can be mentioned. By $(C_1-C_6)$-alkyl is meant the methyl, ethyl, propyl, butyl, pentyl, hexyl radicals and the n-isomers of these radicals.

By alkyloxy radical interrupted by one or more oxygen atoms, is meant preferably radicals of the O—CH$_2$—O—(CH$_2$)$_2$—O—CH$_3$ type.

The bivalent alkylene radicals corresponding to the monovalent radicals mentioned above are for example the methylene, ethylene, 1,3-propylene, 1,2-propylene (=1-methylethylene), 2,3-butylene (=1,2-dimethylethylene), 1,4-butylene, or 1,6-hexylene radicals.

The unsaturated alkyl radicals can contain one or more, for example one, two or three double and/or triple bonds. Of course, an unsaturated alkyl radical contains at least two carbon atoms. By unsaturated alkyl radical is therefore meant for example, the alkenyl radicals such as vinyl, 1-propenyl, allyl, butenyl, 3-methyl-2-butenyl or the alkynyl radicals such as ethynyl, 1-propynyl or propargyl.

By unsaturated bivalent alkylene radicals is meant the alkenylene and alkynylene radicals which can also be linear or branched. These are for example vinylene, propenylene, ethynylene or propynylene radicals.

The cycloalkyl radicals can be monocyclic, bicyclic or tricyclic. These are for example cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl radicals which can optionally be substituted for example by an alkyl containing from 1 to 4 carbon atoms. As substituted cycloalkyl radicals, 4-methylcyclohexyl, 2,3-dimethylcyclohexyl, dimethylcyclopropane and dichlorocyclopropane can be mentioned.

Unless otherwise indicated, the alkyl or cycloalkyl radicals can be non-substituted or substituted by one or more identical or different radicals chosen from $(C_1-C_6)$-alkyl, $(C_1-C_6)$-alkoxy, hydroxyl, halogen such as fluorine, chlorine and bromine, nitro, amino, trifluoromethyl, mono, —$OCF_3$, cyano, carboxyl, —$SO_3H$, —$OSO_3H$, $PO_3H_2$, $OPO_3H_2$, $(C_1-C_4)$— alkoxycarbonyl, phenyl, phenoxy, benzyl and benzyloxy. Of course this also applies when the alkyl radical forms part of a group containing it, for example such as $(C_1-C_6)$-alkyloxycarbonyl, $(C_1-C_6)$-alkylcarbonyl or $(C_1-C_6)$-alkylaminocarbonyl.

By halogen is meant fluorine, chlorine, bromine or iodine.
By the term aryl is meant:
either the heterocyclic $(C_5-C_{14})$-aryl (=$(C_5-C_{14})$-heteroaryl) radicals, in which the carbon atoms of the ring are replaced by a heteroatom such as nitrogen, oxygen or sulphur,
or the carbocyclic $(C_6-C_{14})$-aryl radicals.

Among the carbocyclic $(C_6-C_{14})$-aryl radicals, phenyl, naphthyl, biphenylyl, anthryl or fluorenyl and quite particularly 1-naphthyl, 2-naphthyl and phenyl can be mentioned.

Unless otherwise indicated, the aryl radicals, in particular phenyl, can be non-substituted or substituted by one or more identical or different radicals chosen from $(C_1-C_6)$-alkyl, $(C_1-C_6)$-alkoxy, hydroxyl, hydroxy$(C_1-C_6)$-alkyl, halogen such as fluorine, chlorine and bromine, nitro, amino, trifluoromethyl, —$OCF_3$, cyano, carboxyl, —$SO_3H$, —$OSO_3H$, $PO_3H_2$, $OPO_3H_2$, $(C_1-C_4)$-alkoxycarbonyl, phenyl, phenoxy, benzyl, benzyloxy and methylenedioxy.

In the case of monosubstituted phenyl, the substituent can be situated in position 2, 3 or 4, and preferably in position 3 or 4. Preferably, $Ar^3$ represents a phenyl substituted in position 4. In the case where the phenyl is di-substituted, the substituents can be in positions 2,3 or 2,4 or 2,5 or 2,6 or 3,4 or 3,5. Preferably, when $Ar^1$ represents a di-substituted phenyl, the two substituents are in positions 2,4. When this phenyl is tri-substituted the positions are as follows: 2,3,4 or 2,3,5 or 2,3,6 or 2,4,5 or 2,4,6 or 3,4,5. In the same manner, the naphthyl radicals or other aryl radicals can be substituted in any position, for example the 1-naphthyl radical in positions 2-, 3-, 4-, 5-, 6-, 7-, and 8 and the 2-naphthyl radical in positions 1-, 3-, 4-, 5-, 6-, and 7.

The $(C_5-C_{14})$-aryl group can also represent a monocyclic or polycyclic aromatic system in which 1, 2, 3 or 4 of the carbon atoms of the ring are replaced by heteroatoms, in particular identical or different heteroatoms from the group constituted by nitrogen, oxygen and sulphur. Among the heterocyclic $(C_5-C_{14})$-aryl (=$(C_5-C_{14})$-heteroaryl) groups, the 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups can be mentioned, or also benzocondensed, cyclopenta-, cyclohexa-, or cyclohepta-condensed derivatives of these radicals.

The heterocyclic system can be substituted by the same substituents mentioned above for the carbocyclic system. Of course, the above description concerning the aryl groups also applies when aryl is a radical included in a group such as aryl-alkyl. As preferred examples of aryl-alkyl groups, benzyl, 1-phenylethyl or 2-phenylethyl can be mentioned.

By heterocycle, is preferably meant a non-aromatic radical with 5 or 6 members, optionally containing one or two double bonds and one or more nitrogen or oxygen atoms substituted or non-substituted by the same substituents mentioned above for the carbocyclic system as well as the oxo radical. The invention thus comprises the following heterocycles:

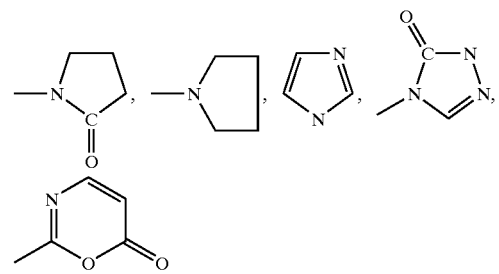

These heterocycles being able to be substituted. The radicals can then be as follows:

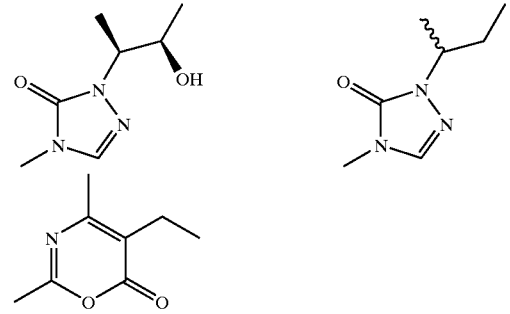

The optically active carbon atoms contained in the compounds of formula (I) can independently of one another have the R configuration or the S configuration.

The compounds of formula (I) can be in the form of pure enantiomers or pure diastereoisomers or in the form of a mixture of enantiomers, for example in the form of racemates or mixtures of diastereoisomers.

A subject of the present invention is therefore pure enantiomers, mixtures of these enantiomers, pure diastereoisomers and mixtures of these diastereoisomers.

The invention comprises mixtures of two or more than two stereoisomers of formula (I) and all the ratios of these stereoisomers in said mixtures.

The compounds of formula (I) can, if appropriate, be present in the form of E isomers or Z isomers. A subject of the invention is therefore pure E isomers, pure Z isomers and E/Z mixtures in any ratio. When the compounds of formula (I) contain a cyclopropane, these compounds of formula (I) can be present in the form of cis or trans isomers. A subject of the invention is therefore pure cis isomers, pure trans isomers and cis/trans mixtures in any ratio.

The invention also comprises all the tautomeric forms of the compounds of Formula (I). The diastereoisomers, including the E/Z (or cis/trans) isomers can be separated into individual isomers, for example by chromatography. The racemates can be separated into two enantiomers by standard methods such as chiral-phase chromatography or by resolution methods.

The physiologically acceptable salts of the compounds of formula (I) are in particular pharmaceutically useful or non-toxic salts or physiologically useful salts.

When the compounds of formula (I) contain an acid group such as carboxylic acid, these are for example alkali metal or alkaline-earth salts such as sodium, potassium, magnesium, calcium salts, and also salts formed with physiologically acceptable quaternary ammonium ions and the addition salts with acids such as ammonia and physiologically acceptable organic amines such as for example triethylamine, ethanolamine or tris-(2-hydroxyethyl)amine.

When the compounds of formula (I) contain a basic group, they can form an addition salt with acids, for example with inorganic acids such as hydrochloric, sulphuric, phosphoric acid or with carboxylic organic acids such as acetic, trifluoroacetic, citric, benzoic, maleic, fumaric, tartaric, methanesulphonic or para toluene sulphonic acid.

The compounds of formula (I) which comprise a basic group and an acid group, such as for example guanidino and carboxylic, can be present in the form of zwitterions (betaines), which are also included in the present invention.

When the compounds of formula (I) contain a charged ammonium group, the counter anion (Q⁻) is preferably a monovalent anion or a polyvalent anion equivalent of a physiologically acceptable and in particular pharmaceutically acceptable non toxic organic or inorganic acid, for example the anion or an anion equivalent of one of the acids mentioned above, which is useful for the formation of the addition salts. Q⁻ can be for example one of the anions (or anion equivalents) of a group chosen from chlorine, sulphate, phosphate, acetate, trifluoroacetate, citrate, benzoate, maleate, fumarate, tartrate, methanesulphonate and paratoluenesulphonate.

The salts of the compounds of formula (I) can be obtained by ordinary methods known to a person skilled in the art, for example by combining a compound of formula (I) with an organic or inorganic acid or a base in a solvent or a dispersant or from another salt by cation or anion exchange.

The invention also includes all the salts of the compounds of formula (I) which, because of their low physiological acceptability, cannot be used directly as a medicament, but are useful as intermediate products for use in later chemical modifications to the compounds of formula (I) or as starting products for the preparation of physiologically acceptable salts.

The present invention also includes all the solvates of the compounds of formula (I) for examples hydrates, solvates formed with alcohols, and all the derivatives of the compounds of Formula (I), for example esters, prodrugs and other physiologically acceptable derivatives, as well as the metabolites of the compounds of Formula (I).

A subject of the invention is also the prodrugs of the compounds of formula (I) which can be converted to compounds of formula (I) in vivo under physiological conditions. The prodrugs of the compounds of Formula (I), namely the derivatives of the compounds of formula (I) chemically modified in order to obtain properties improved in the desired manner, are known to a person skilled in the art.

In order to have more information on the type of prodrug envisaged in the present invention, the following works can be mentioned: Fleicher et al., Advanced Drug Delivery Review 19 (1996) 115–130; Design of prodrugs, H. Bundgaard, Ed., Elsevier, 1985; H. Bungaard, Drugs of the Future 16 (1991) 443; Saulnier et al. Bioorg. Med. Chem. Lett. 4 (1994) 1985; Safadi et al. Pharmaceutical Res. 10 (1993) 1350. Among the appropriate prodrugs of the compounds of formula (I) the following can preferably be mentioned:

the prodrugs in the form of esters of the carboxylic, sulphonic or phosphonic groups, when, for example, $Ar^3$ is substituted respectively by a —$CO_2H$, —$SO_3H$ or —$PO_3H$ group.

the prodrugs in the form of acyl and carbamate for the groups containing an acylable nitrogen such as the amino or guanidine groups.

the prodrugs in the form of quaternary derivatives of cyclic or non-cyclic (benzyl substituted) nitrogen.

In the prodrugs which are acylated; or in carbamate form, once or more times, for example twice, a hydrogen atom situated on the nitrogen atom is replaced by an acyl or carbamate group. Among the preferred acyl or carbamate groups, the $R_{12}CO$—, $R_{13}OCO$— groups can be mentioned, in which $R_{12}$ is a hydrogen or a $(C_1–C_{18})$-alkyl, $(C_3–C_{14})$-cycloalkyl, $(C_3–C_{14})$-cycloalkyl-$(C_1–C_8)$-alkyl, $(C_5–C_{14})$-aryl radical, in which 1 to 5 carbon atoms can be replaced by heteroatoms such as N, O, S or $(C_5–C_{14})$-aryl-$(C_1–C_8)$ alkyl, in which 1 to 5 carbon atoms in the aryl part can be replaced by heteroatoms such as N, O, S and $R_{13}$ with the same values as $R_{12}$ with the exception of hydrogen.

Of course, $Ar^1$, $Ar^2$, $Ar^3$, $R^1$, $R^2$, $R^3$, $R^4$, $R^5$, $R^6$, $R^7$, $R^8$, $R^9$, $R^{10}$, $R^{11}$, $R^{12}$ and $R^{13}$ can adopt the above definitions independently of one another.

Among the definitions relating to Formula (I), the following preferred values can be mentioned:

$Ar^1$ and $Ar^3$ represent phenyl groups, $Ar^1$ represents a phenyl group and $Ar^3$ represents a heterocycle, A is preferably a methylene group, B is preferably a —$CH_2$—CH=CH— or —$CH_2$-(cyclopropyl)-group, said groups being non-substituted or substituted by one or more halogens or $(C_1–C_4)$-alkyl, $R^1$ is preferably a hydrogen atom or a methyl or ethyl group, non-substituted or substituted by fluorine, —OH, —$NH_2$, $(C_1–C_8)$-alkyloxy, $(C_1–C_8)$-alkylamino, or di-$(C_1–C_8)$-alkylamino, pyrrolidino or 2-oxo-pyrrolidino.

$R^2$ and $R^3$ are preferably halogen atoms $R^4$ is preferably a hydrogen atom $R^6$ is preferably a hydrogen atom $R^5$ and $R^7$ preferably represent hydrogen $R^8$, $R^9$ and $R^{10}$ preferably represent hydrogen, CN, halogen, —$CF_3$, —$OCF_3$, OH, —$SO_3H$, —P(O)(OH)$_2$, Carboxy, —$OSO_3H$, —$OPO_3H$, —$NH_2$, $(C_1–C_6)$-alkyl, a non-aromatic saturated or unsaturated heterocyclic, amino-$(C_1–C_6)$-alkyl, hydroxy-$(C_1–C_6)$-alkyl, $(C_1–C_6)$-alkyloxy, $(C_1–C_6)$-alkylamino-$(C_1–C_6)$-alkyloxy, $(C_1–C_6)$-alkyloxycarbonyl, $(C_1–C_6)$-alkylcarbonyl, $(C_1–C_6)$-alkylaminocarbonyl, $(C_1–C_6)$-alkylamino, di-$(C_1–C_6)$-alkylamino or di-$(C_1–C_6)$-alkylamino-$(C_1–C_6)$-alkyloxy radical, said alkyl radicals or heterocycles being non-substituted or substituted by halogen, OH, $SO_3H$, P(O) (OH)$_2$, oxo, Carboxy, —$OSO_3H$, —$OPO_3H_2$, —$NH_2$, phenyl, $(C_1–C_6)$-alkyl, $(C_1–C_6)$-alkyloxy, hydroxy-$(C_1–C_6)$-alkyl, $(C_1–C_6)$-alkylamino or di-$(C_1–C_6)$-alkylamino.

A more particular subject of the invention is the compounds of formula (I) as defined above in which A is a —$CH_2$— group, B is a —$CH_2$—CH=CH— or —$CH_2$-cyclopropyl-group, $Ar^1$ represents a phenyl and $Ar^2$ represents a phenylene as well as their physiologically acceptable addition salts.

A more particular subject of the invention is the compounds of formula (I) as defined above corresponding to the structure:

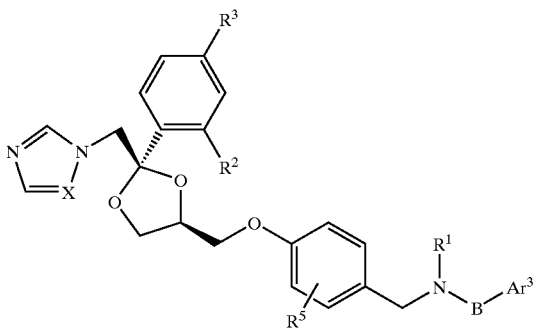

(IA)

in which, B, X, Ar³, R⁵ and R¹ are as defined above and R² and R³ represent a chlorine or fluorine atom as well as their physiologically acceptable addition salts.

A more particular subject of the invention is the compounds of formula (I) or (IA) as defined above in which $R_2$ and $R_3$ are fluorine or chlorine atoms, X represents CH or N and Ar³ represents a phenyl group, non-substituted or substituted by $R^8$ as defined previously, as well as their physiologically acceptable addition salts.

A quite particular subject of the invention is the compounds of formula (I) or (IA) as defined previously, in which $R^1$ is a hydrogen atom or a methyl, or ethyl group, non-substituted or substituted by an F, OH, $NH_2$, $(C_1-C_6)$-alkyloxy, $(C_1-C_6)$-alkylamino, di-$(C_1-C_6)$-alkylamino, pyrrolidino or 2-oxo-pyrrolidino group as well as their physiologically acceptable addition salts.

A quite particular subject of the invention is the compounds of Formula (IA) as defined previously in which Ar³ is a phenyl, non-substituted or substituted by $R^8$ representing a —Cl, —F, CN, —CF₃, —OCF₃, —OH, —NH₂, $(C_1-C_6)$-alkyloxy, $(C_1-C_6)$-alkylamino, di-$(C_1-C_6)$-alkylamino radical or a heterocycle chosen from:

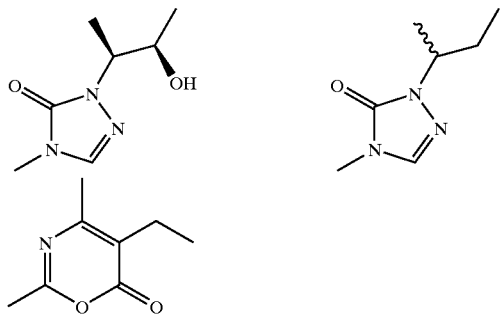

A quite particular subject of the invention is the following compounds:

cis-4-[[2-(2,4-dichlorophenyl)-2-(1H-imidazol-1-ylmethyl)-1,3-dioxolan-4-yl]methoxy]-N-methyl-N-(3-phenyl-2(E)-propenyl)-benzenemethanamine 4-[[2-(2,4-dichlorophenyl)-2-(1H-imidazol-1-ylmethyl)-1,3-dioxolan-4-yl]methoxy]-N-methyl-N-[3-(4-chlorophenyl-2(E)-propenyl]-1-benzenemethanamine cis-4-[3-[[[4-[[2-(2,4-dichlorophenyl)-2-(1H-imidazol-1-ylmethyl)-1,3-dioxan-4-yl]methoxy]phenyl]methyl]methylamino]-1(E)-propenyl]-phenol cis-4-[[2-(2,4-dichlorophenyl)-2-(1H-imidazol-1-ylmethyl)-1,3-dioxolan-4-yl]methoxy]-N-(3-phenyl-2(E)-propenyl)-benzenemethanamine cis-4-[3-[[[4-[[2-(2,4-dichlorophenyl)-2-(1H-imidazol-1-ylmethyl)-1,3-dioxan-4-yl]methoxy]phenyl]methyl]methylamino]-1(E)-propenyl]-phenol 4-[[2-(2,4-dichlorophenyl)-2-(1H-imidazol-1-ylmethyl)-1,3-dioxolan-4-yl]methoxy]-N-methyl-N-(3-phenyl-2(E)-propenyl)-1-naphthalenemethanamine phosphate and trifluoroacetate cis-4-[[2-(2,4-dichlorophenyl)-2-(1H-imidazol-1-ylmethyl)-1,3-dioxolan-4-yl]methoxy]-N-(3-phenyl-2(E)-propenyl)-4-chloro-benzenemethanamine cis-N-(2-aminoethyl)-4-[[2-(2,4-dichlorophenyl)-2-(1H-imidazol-1-ylmethyl)-1,3-dioxolan-4-yl]methoxy]-N-(3-phenyl-2(E)-propenyl)-benzenemethanamine trifluoroacetate cis-N-(2-aminoethyl)-N-[3-(4-chlorophenyl)-2(E)-propenyl]-4-[[2-(2,4-dichlorophenyl)-2-(1H-imidazol-1-ylmethyl)-1,3-dioxolan-4-yl]methoxy]-benzenemethanamine cis-2-[[[4-[[2-(2,4-dichlorophenyl)-2-(1H-imidazol-1-ylmethyl)-1,3-dioxolan-4-yl]methoxy]phenyl]methyl](3-phenyl-2(E)-propenyl)amino]-ethanol A subject of the invention is also a process for the preparation of compounds of formula (I) characterized in that a compound of formula (II):

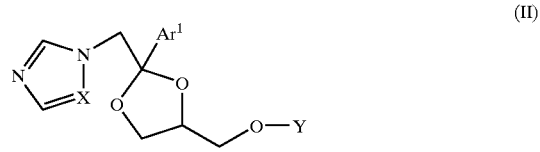

(II)

in which Y represents a leaving group after nucleophilic substitution such as mesylate or tosylate and the other substituents retain their previous meaning, is subjected to the action, in the presence of a base, of a compound of formula (III):

HO—Ar²—A—N(R¹)—B—Ar³ (III)

in which Ar², A, R¹, B and Ar³ retain their previous meaning, in order to obtain the corresponding compound of formula (I).

This reaction is carried out under standard nucleophilic substitution conditions of the R—OH+R'—OTs-->R—O—R' type known to a person skilled in the art, Ts being a tosyl group. The base used can in particular be sodium hydride and the solvent can be DMF.

The compounds of formula (II) used as starting products are products known generally, in particular when Ar¹ is a phenyl. They can be prepared according to the process indicated in *J. Med. Chem.* (1979) 22(8) 1003.

Certain compounds of formula (III) (R¹=Me) are easily accessible. They can be prepared as indicated in the diagram below or in the experimental part:

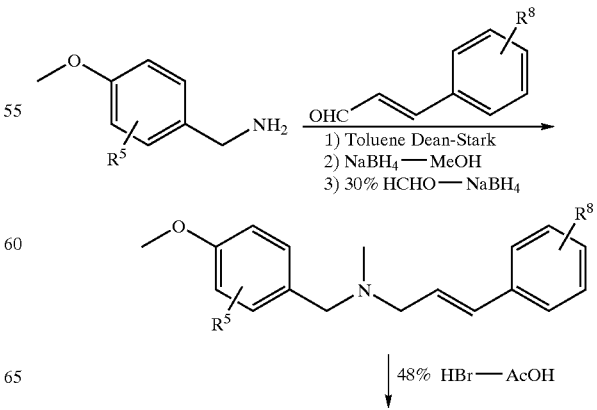

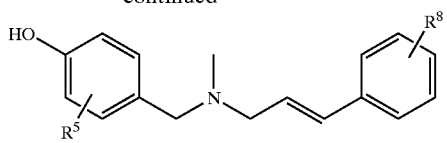

As a variant process, the compound of formula (II) is reacted with an aryl of formula (III') HO—C$_4$H$_6$—CHO in the presence of a base, the phenyl being non-substituted or substituted by R$^5$, in order to obtain a compound of formula (IIa):

(IIa)

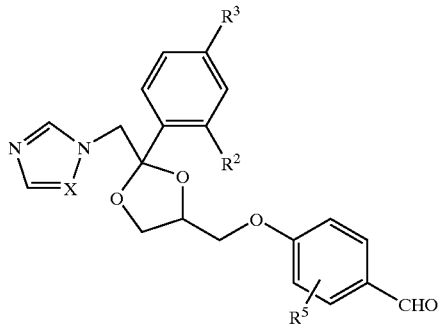

which is reacted with an R$_1$—NH$_2$ amine, R$^1$ being as defined previously, followed by a reduction reaction in the presence of a reducing agent such as NaBH$_3$CN, in order to obtain the amine of formula (IIb):

(IIb)

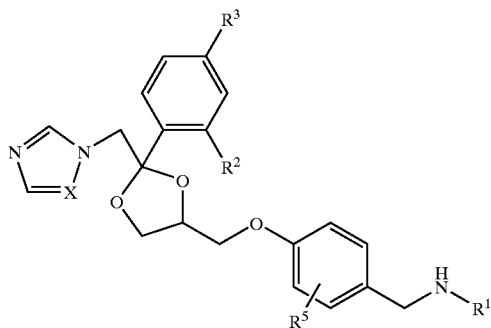

which is reacted
either with a derivative of formula:
OHC—CH═CH—C$_6$H$_4$—R$^8$ or OHC—(Cyclopropyl)-C$_6$H$_4$—R$^8$ followed by a reduction reaction in the presence of a reducing agent such as NaBH$_3$CN or pyridine.BH$_3$
or with a compound of formula:
AcO-CH$_2$—CH═CH—C$_6$H$_4$—RB
in the presence of a palladium derivative
in order to obtain the following compounds of formulae (IAA) and (IAB):

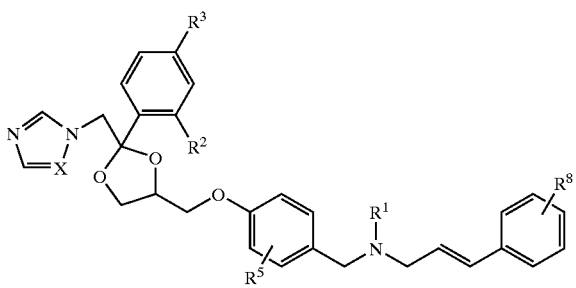

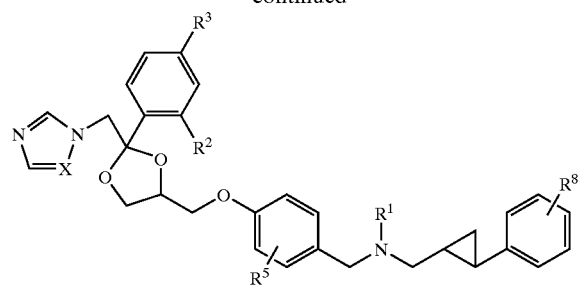

The first reducing amination reaction involving aldehyde (IIa) is carried out preferably in the presence of reagents such as NaBH$_3$CN in methanol or pyridin.BH$_3$. The second reducing amination reaction involving amine (IIc) with a trans-cinnamaldehyde derivative, is also carried out preferably in the presence of NaBH$_3$CN in methanol. The reaction involving the amine (IIc) with an allyl acetate is carried out in the presence of a palladium derivative, for example in acetonitrile/water medium (tppts/Pd(OAc)$_2$).

Preferably, the compound of formula (IIa) is reacted with an amine of formula R'$^1$—(CH$_2$)$_2$—NH$_2$, R$^{11}$ representing an F, OH group, an amine or an alkylamine, being suitably protected (such as NHCO$_2$tbu, pyrrolidino, 2-oxo-pyrrolidino), or a dialkylamine in order to obtain a compound of formula (IIc), in the presence of a reducing agent such as NaBH$_3$CN:

(IIc)

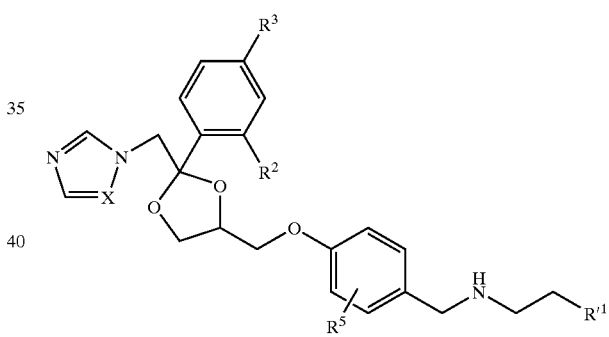

which is reacted with a conjugated aldehyde as defined previously (OHC—CH═CH—C$_4$H$_6$—R$^8$), in the presence of a reducing agent such as NaBH$_3$CN, in order to obtain a compound of formula (IAB):

(IAB)

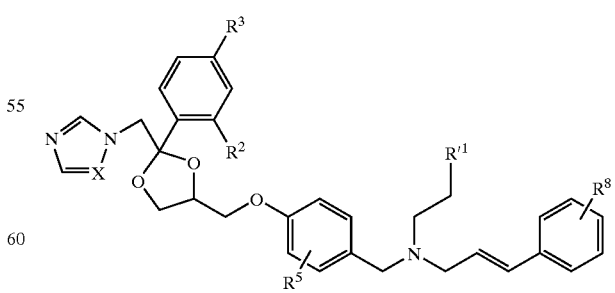

The starting compounds of formula (II) or (III) can be prepared according to processes described in the literature or are also accessible by analogy. The preparation of the compounds of formula (II) is described in *Eur. J. Med.*

Chem. (1995) 30, 617–626 or *J. Heterocyclic Chemistry* (1990), 27 2053, it being understood that the present invention is not restricted to these syntheses or to these starting products. There is no major difficulty for a person skilled in the art to provide modifications to the syntheses described in our application for the preparation of other compounds of formula (I) according to the invention.

The compounds of formula (I) are compounds having a pharmacological activity and can thus be used as medicaments, in particular as antifungals.

A subject of the present invention is therefore the compounds of formula (I) and/or their physiologically acceptable salts and/or their prodrugs as medicaments.

The compounds of formula (I) as well as their physiologically acceptable salts and their prodrugs can be administered to animals, preferably to mammals and in particular to human beings as therapeutic or prophylactic medicaments.

The compounds of formula (I) have useful antifungal properties. They are in particular active on *Candida albicans* and other *Candidas* such as *Candida glabrata, krusei, tropicalis, pseudotropicalis* and *parapsilosis*, on *Aspergillus, Aspergillus flavus, Aspergillus niger, Cryptococcus neoformans, Microsporum canis, Trichophyton rubrun, Trichophyton mentagrophyte*.

The compounds of formula (I) can be used as medicaments in humans or animals, in particular to combat digestive, urinary, vaginal or cutaneous candidoses, cryptococcoses, for example neuromeningeal, pulmonary or cutaneous cryptococcoses, bronchopulmonary and pulmonary aspergilloses and invasive aspergilloses in immunodeficient individuals.

The compounds according to the invention can also be used in the prevention of mycosic diseases in individuals with congenital or acquired immunodeficiency.

The compounds of the invention are not limited to a pharmaceutical use. They can be also used as fungicides in fields other than that of pharmaceuticals.

A subject of the invention is therefore, as antifungal medicaments, the compounds of formula (I).

A subject of the invention is also the use of chemical entities having at one end the following groups:

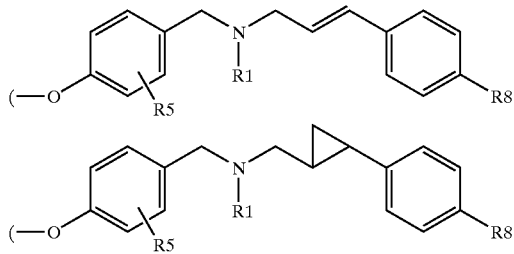

and at the other end a pharmacophore group having a fungicidal activity, for example an azole or triazole derivative as defined previously, for the preparation of medicaments having an antifungal activity.

The compounds according to the invention can be administered as they are or in a mixture with one or more other compounds of formula (I) or also in the form of a pharmaceutical preparation (pharmaceutical composition) which allows an enteral or parenteral administration and which contains as active ingredient an effective dose of at least one compound of formula (I) and/or its physiologically acceptable salts and/or its prodrugs as well as standard and pharmaceutically inert supports and/or additives.

The pharmaceutical compositions according to the invention allow enteral or parenteral administration, containing as active ingredient an effective dose of at least one compound of formula (I) and/or its physiologically acceptable salts and/or its prodrugs as well as one or more pharmaceutically inert supports, and/or one or more usual additives.

A subject of the invention is therefore the pharmaceutical compositions containing a compound of formula (I) as defined previously as well as a vehicle.

The medicaments can be administered orally, for example in the form of pills, tablets, coated tablets, flakes, granules, gelatin capsules and soft capsules, solutions, syrups, emulsions, suspensions or aerosol mixtures.

The administration can however be carried out by rectal route, for example in the form of suppositories, by parenteral route, for example in the form of injectable solutions or infusions, microcapsules or implants, by percutaneous route, for example in the form of ointments, solutions, pigments or colouring agents, by transdermal route in the form of patches or by other routes such as in the form of nasal aerosols or sprays.

The pharmaceutical compositions according to the invention are prepared according to methods known per se, pharmaceutically inert organic or inorganic supports being added to the compounds of formula (I) and/or their physiologically acceptable salts and/or their prodrugs. For the production of pills, tablets, coated tablets and hard gelatin capsules, it is possible to use for example, lactose, corn starch or its derivatives, talc, stearic acid or its salts, etc. Suitable supports for soft gelatin capsules or suppositories are for example fats, waxes, semi-solid or liquid polyols, natural or modified oils etc. Appropriate vehicles for the preparation of solutions, for example injectable solutions, emulsions or syrups are for example water, alcohols, glycerol, polyols, sucrose, inverted sugars, glucose, vegetable oils, etc. Suitable supports for microcapsules or implants are for example glyoxylic acid and lactic acid copolymers. The pharmaceutical preparations normally contain from 0.5% to 90% by weight of compounds of formula (I) and/or their physiologically acceptable salts.

In addition to the active ingredients and supports, the pharmaceutical preparations can contain additives such as for example diluents, disintegrating agents, binders, lubricants, wetting agents, stabilizers, emulsifiers, preservatives, sweeteners, colouring agents, flavouring agents, thickeners, buffering agents, and also solvents or solubilizers or agents for obtaining a delayed effect and also salts for modifying the osmotic pressure, coating agents or antioxidants. They can also contain two or more compounds of formula (I) and/or their physiologically acceptable salts and/or their prodrugs. Moreover, in more than at least one or more compounds of formula (I) and/or their physiologically acceptable salts and/or their prodrugs, they can contain at least one or more other useful active ingredients as therapeutics or prophylactics.

The pharmaceutical preparations (pharmaceutical compositions) normally contain from 0.2 to 500 mg, and preferably from 1 to 200 mg of the compound of formula (I) and/or their physiologically acceptable salts and/or their prodrugs.

A more particular subject of the present invention is therefore a compound of formula (I) and/or its physiologically acceptable salts and/or its prodrugs as defined above as a medicament having an antifungal activity.

A subject of the present invention is also the use of the compounds of formula (I) and/or their physiologically acceptable salts and/or their prodrugs as defined above for the preparation of antifungal medicaments.

When the compounds of formula (I) are used, the doses can vary within broad limits and must be fixed as a function of the person to be treated. This depends for example on the compound used or the nature and severity of the disease to be treated and whether serious or chronic conditions prevail or a prophylactic treatment is being implemented.

In the case of administration by oral route, the daily dose generally varies from 0.01 to 100 mg/kg and preferably from 0.1 to 50 mg/kg, in particular from 0.1 to 5 mg/kg.

In the case of administration by intravenous route, the daily dose varies approximately from 0.01 to 100 mg/kg and preferably from 0.05 to 10 mg/kg.

The daily dose can be divided, in particular in the case of the administration of a large quantity of active ingredient, into several, for example 2, 3 or 4 parts. If appropriate, as a function of individual behaviour, it can be necessary to administer the different doses in an increasing or decreasing manner.

The compounds of formula (I) and their salts can also be used as intermediates for the preparation of other compounds, in particular other active ingredients, which are accessible from the compounds of formula (I), for example by modification or introduction of radicals or functional groups.

Finally, a subject of the invention is intermediate compounds of the processes as defined previously, the compounds of formulae (IIa), (IIb), and (IIc).

EXAMPLES

The products were identified by mass spectrum (MS), infrared (IR) and/or NMR spectrum. The compounds were purified by normal-phase (in particular in the presence of a $CH_2Cl_2$/MeOH mixture) or in reversed-phase chromatography (in the presence of acetic or trifluoroacetic acid). The compounds of formula (I) purified using an eluent which contains for example trifluoroacetic acid, and which are then dried or in which, during the last synthesis stage, for example trifluoroacetic acid was used in order to eliminate a tert-butyl protective group, sometimes contain, depending on the manner in which the product was dried, the acid originating from the eluent or the last synthesis stage and are therefore found partially or completely in the form of the salt of the acid used, for example in the form of an acetic or trifluoroacetic acid salt. They can also be more or less hydrated.

Abbreviations/chemical names optionally used:

AcOEt: ethyl acetate; DMF: dimethylformamide; HOBt: 1-hydroxybenzotriazole hydrate, MeOH: methanol; TEA: triethylamine; TFA: trifluoroacetic acid; THF: tetrahydrofuran; MCPBA: meta-chloroperoxybenzoic acid; DBU: 1,8-diazabicyclo[5.4.0]undec-7-ene; PTSA: paratoluenesulphonic acid; DPPA: diphenylphosphorylazide; DMSO: dimethylsulphoxide; Pd/C Palladium on carbon; Boc: terbutoxycarbonyl; CBz: benzyloxycarbonyl; DCC 1,3-dicyclohexylcarbodiimide;

IR: Infrared; NMR: Nuclear Magnetic Resonance; MS: Mass Spectrum; PES: Positive mode electrospray; sh.: shoulder; S: strong; s: singlet; d: doublet; t: triplet; quad: quadruplet; quint: quintuplet; b: broad; m: multiplet; J: coupling constant; Rf: retention factor (chromatography).

The NMR spectra below were interpreted and the aromatic hydrogens are identified thus:

Preparation 1: 4-hydroxy-N-methyl-N-(3-phenyl-2 (E)-propenyl)-benzenemethanamine (P1)

Stage a): 4-methoxy-N-methyl-N-(3-phenyl-2(E)-propenyl)-benzenemethanamine

A solution constituted by trans-cinnamaldehyde (Jansen, d=1.048, 13.2 g, 0.1 mol) and 4-methoxybenzylamine (Fluka, d=1.057, 13.7 g, 0.1 mol) in 250 ml of toluene is heated to reflux for 2 hours 30 minutes, whilst eliminating the water formed during the reaction using a "Dean-Stark" apparatus, then the toluene is evaporated off under reduced pressure. The residue obtained (Schiff base) is then solubilized in 150 ml of methanol, then the Schiff base is reduced by adding 3.8 g of $NaBH_4$ at 40° C. Finally, 81 ml of 37% formaldehyde is added to the reaction medium (amino reduction reaction), the mixture is taken to reflux for 30 minutes and stirred overnight at ambient temperature. After evaporation of the methanol, the residue is taken up with dichloromethane, washed twice with water and once with a saturated aqueous solution of NaCl, dried over $MgSO_4$, filtered and evaporated under reduced pressure until a dry extract is obtained which is purified by chromatography on silica eluting with a $CH_2Cl_2$/AcOEt mixture 70/30. 9.07 g of expected crystallized product is obtained. Rf 0.20 $CH_2Cl_2$/AcOEt 70/30.

NMR 1H (300 MHz $CDCl_3$) 2.23 (s, 3H, $CH_3$—N); 3.18 (dl, 2H, N—C$\underline{H}_2$—CH=CH—Ph); 6.31 (td, J=16; 6.5 Hz, N—$CH_2$—C$\underline{H}$=CH—Ph); 6.54 (d, 1H, J=16 Hz, N—$CH_2$—CH=C$\underline{H}$—Ph); 3.49 (s, 2H, Ph—C$\underline{H}_2$—N); 3.80 (s, 3H, Ph—O—C$\underline{H}_3$); 6.86 and 7, 25 AA'BB'; 7.31 (bt, 2H, H meta); 7.38 (bd, 2H, H ortho); 7.24 (masked 1H, H para).

Stage b): 4-hydroxy-N-methyl-N-(3-phenyl-2(E)-propenyl)-benzenemethanamine 20 ml of 48% hydrobromic acid is added to a solution of the product prepared in the previous stage (1 g, 3.74 mmol) in 20 ml of acetic acid, and heated to reflux for 5 hours and 30 minutes. After evaporation under reduced pressure by entraining the water with ethyl acetate, a dry extract is obtained, which is purified by chromatography on silica eluting with a $CH_2Cl_2$/MeOH 95/5 mixture in order to obtain 660 mg of expected product. Rf 0.46 $CH_2Cl_2$/MeOH 95/5.

Preparations 2 and 3: 4-[cis-[2-(2,4-dichlorophenyl)-2-(1H-imidazol-1-ylmethyl)-1,3-dioxolan-4-yl methoxy]-N-methyl-benzenemethanamine Stage a): 4-[cis-[2-(2,4-dichlorophenyl)-2-(1H-imidazol-1-ylmethyl)-1,3-dioxolan-4-yl]methoxy]-benzaldehyde (P2)

A solution of 4-hydroxybenzaldehyde (4.59 g, 0.0376 mol) in 80 ml of DMF is added to a suspension of NaH (1.723 g) in DMF (150 ml) and stirred for 30 minutes at ambient temperature. Then 20 g of (cis-[2-(2,4-dichlorophenyl)-2-(1H-imidazol-1-ylmethyl)-1,3-dioxolan-4-yl)methyl] 4-methyl-benzenesulphonate is added and heated overnight at 90° C. After returning to ambient temperature, the reaction medium is poured into 500 ml of water and extracted with 4 times 300 ml of dichloromethane, the organic phases are washed with water saturated in NaCl, the organic phase is dried over $MgSO_4$, filtered and evaporated under reduced pressure until a dry extract is obtained which is taken up in 40 ml of ether. Crystallization is observed. The crystals are separated, rinsed and washed with 4 times 20 ml of ether. 14.48 g of expected product is obtained (as well as 5.84 g of product recovered in the mother liquors). Rf 0.18 $CH_2Cl_2$/MeOH 98/2.

NMR 300 MHz $CDCl_3$ 3.35 (dd) and 3.77 (dd) 2H, 3.80 (dd) and 3.91 (dd) 2H: O—C$\underline{H}_2$—CH—C$\underline{H}_2$—O; 4.41 (m, 1H O—$CH_2$—C$\underline{H}$—$CH_2$—O); 4.45 and 4.55 (AB, 2N, N—$CH_2$-Cq); 6.42 and 7.85 (AA'BB') 9.90 (s, 1H, C$\underline{H}$O); 7.03 (dl, 2H, $H_4$ and $H_5$); 7.29 (dd, 1H, Hb); 7.49 (d, 1H, Ha); 7.61 (d, 1H, Hc); 7.70 (s, 1H, H2).

Stage b): 4-[cis-[2-(2,4-dichlorophenyl)-2-(1H-imidazol-1-ylmethyl)-1,3-dioxolan-4-yl]methoxy]-N-methyl-benzenemethanamine (amino-reduction) (P3)

Methylamine hydrochloride (8.833 g, 0.131 mol) and $NaBH_3CN$ (1.654 g, 0.026 mol) are added to a solution of the product P2 prepared in the previous stage (5.70 g; 0.0131 mol) in methanol (170 ml), and stirring is carried out for 19 hours, followed by evaporation under reduced pressure until a dry extract is obtained, and taking up in a water/$CH_2Cl_2$/NaOH 2N (50 ml/20 ml/70 ml) mixture; the aqueous phase is reextracted with 70 ml of dichloromethane, washed with water saturated in NaCl, dried over MgSO4, filtered and evaporated under reduced pressure in order to obtain 6.1 g of expected crude product which is purified by chromatography on silica eluting with a $CH_2Cl_2$/MeOH mixture 95/5 then $CH_2Cl_2$/MeOH 87/13 to which 1% of TEA is added. 4.2 g of expected pure product is obtained. Rf 0.46 $CH_2Cl_2$/MeOH 90/10.

NMR (300 MHz, $CDCl_3$) 2.44 (s, 3H, N—C$\underline{H}_3$); 3.33 (dd) and 3.76 (dd) 2H, 3.73 (dd) and 3.88 (dd) 2H:: O—C$\underline{H}_2$—CH—C$\underline{H}_2$—O; 4.35 (m, 1H, O—$CH_2$—C$\underline{H}$—$CH_2$—O); 3.68 (s, 2H, N—C$\underline{H}_2$-Cq); 4.45 (AB, 2H); 6.78 and 7, 23 (AA'BB'); 7.46 (d, 1H, Ha); 7.26 (dd, 1H, Hb); 7.58 (d, 1H, Hc); 7.50 (s, 1H, H2). 6.98 (d, 2H, H4 and H5).

Preparation 4: 3-[4-[(2-methoxyethoxy)methoxy]phenyl]-2(E)-propenal

Stage a) Protection: 4-[(2-methoxyethoxy)methoxy]-benzaldehyde

Diisopropylamine (70 ml, 0.4 mol) is added to a solution of 4-hydroxybenzaldehyde (24.4 g, 0.2 mol) in 500 ml of acetonitrile, and cooled down to approximately 9° C. Then MEM chloride (40.30 ml, 0.4 mol over 30 minutes) is added, the reaction medium is allowed to return to ambient temperature for 1 hour and evaporated under reduced pressure until a residue is obtained which is taken up in 500 ml of dichloromethane. The organic phase is washed with 2N hydrochloric acid (2×500 ml) then with 1N aqueous soda (2×500 ml) and finally with water saturated in NaCl. The organic phase is then dried over $MgSO_4$, filtered and dried. 41.322 g of expected product (oil) is obtained. Rf 0.32 Cyclohexane/ethyl acetate 70/30.

NMR 300 MHz $CDCl_3$ 3.38 (s, 3H, C$\underline{H}_3$—O—$(CH_2)_2$—O—$CH_2$—O); 3.57 (m) and 3.89 (m) 4H $CH_3$—O—(C$\underline{H}_2)_2$—O—$CH_2$—O); 5.36 (s, 2H, $CH_3$—O—$(CH_2)_2$—O—C$\underline{H}_2$—O)); 7.18 and 7.85 (AA'BB'); 4.92 (s, 1H, C$\underline{H}$O).

Stage b) Wittig: Ethyl 3-[4-[(2-ethoxyethoxy)methoxy]phenyl]-2 (E)-propenoate 11 ml of TEA is added to a solution constituted by (diethoxyphosphinyl)-ethyl acetate (15.8 ml, 0.0786 mol), and 99% LiBr (6.895 g, 0.0786 mol) in 100 ml of THF, followed by stirring for 10 minutes then the derivative prepared above (15 g, 0.0714 mol) in THF (55 ml) is added. The reaction medium is stirred for 12 hours, filtered in order to eliminate the TEA salt, then evaporated under reduced pressure until a dry extract is obtained which is taken up in dichloromethane (200 ml), followed by washing with hydrochloric acid then with a saturated aqueous solution of NaCl. The organic phase is dried over $MgSO_4$, filtered and dried in order to obtain a crude product which is purified by chromatography on silica eluting with an AcOEt/Cyclohexane 30/70 mixture. 13.02 g of the expected purified product is obtained. Rf 0.43 Cyclohexane/ethyl acetate 70/30.

NMR 300 MHz $CDCl_3$ 1.33 (t, 3H, C$\underline{H}_3$—$CH_2$—O); 4.25 (q, 2H, $CH_3$—C$\underline{H}_2$—O); 3.37 (s, 3H, C$\underline{H}_3$—O—$(CH_2)_2$—O—$CH_2$—O); 3.55 (m) and 3.82 (m, 4H, $CH_3$—O—(C$\underline{H}_2)^2$—O—$CH_2$—O); 5.30 (s, 2H, $CH_3$—O—$(CH_2)_2$—O—C$\underline{H}_2$—O)); 6.32 (d, 1H), 7.64 (d, 1H): Ph—CH=CH—CO; 7.05 and 7.47 AA'BB'.

Stage c) Reduction: 3-[4-[(2-methoxyethoxy)methoxy]phenyl]-2(E)-propen-1-ol DIBAL (65 ml at 1M in dichloromethane then 6.5 ml at 1.5 mol in toluene) is added to a solution of the derivative prepared in the previous stage (10 g, 0.0357 mol) in 100 ml of dichloromethane cooled down to −60° C., and stirred for 1 hour at −60° C. The temperature is then allowed to return to −10° C. after having added 40 ml of ethyl acetate and the reaction medium is poured into a 1M solution of potassium and sodium tartrate (750 ml). 550 ml of dichloromethane is added, followed by washing and drying in order to obtain 8.734 g of crude product which is purified by chromatography on silica eluting with a dichloromethane/methanol mixture 98/2. 8.287 g of the expected purified product is obtained. Rf 0.14 cyclohexane/ethyl acetate 70/30.

NMR 300 MHz $CDCl_3$ 1.41 (bt, 1H, $\underline{H}$O—$CH_2$—CH=CH—Ph); 4.30 (1, 2H, HO—C$\underline{H}_2$—CH=CH—Ph); 6.25 (td, 1H, J=6, 16 Hz, HO—$CH_2$—C$\underline{H}$=CH—Ph); 6.56 (bd, 1H, J=16 Hz, HO—$CH_2$—CH=C$\underline{H}$—Ph); 3.37 (s, 3H, C$\underline{H}_3$—O—$(CH_2)_2$—O—$CH_2$—O); 3.56 (m) and 3.82 (m) 4H $CH_3$—O—(C$\underline{H}_2)_2$—O—$CH_2$-o; 5.27 (bs, 2H, $CH_3$—O—$(CH_2)_2$—O—C$\underline{H}_2$—O); 7.01 and 7.32 AA'BB'.

Stage d) Oxidation: 3-[4-[(2-methoxyethoxy)methoxy]phenyl]-2(E)-propenal

The mixture constituted by (I) (8 g, 0.034 mol) and $MnO_2$ (28.9 g, 0.34 mol) in dichloromethane 80 ml, is stirred overnight, filtered and evaporated under reduced pressure until 7.668 g of an oil corresponding to the expected product is obtained. Rf 0.38 Cyclohexane/ethyl acetate 60/40.

Preparation 5: cis-4-[[2-(2,4-dichlorophenyl)-2-(1H-imidazol-1-ylmethyl)-1,3-dioxolan-4-yl methoxy]-N-methyl-1-naphthalenemethanamine

Stage a) Coupling: cis-4-[[2-(2,4-dichlorophenyl)-2-(1H-imidazol-1-ylmethyl)-1,3-dioxolan-4-yl]methoxy]-1-naphthalenecarboxaldehyde 4-hydroxy-1-naphthalenecarboxaldehyde (860 mg, 5 mmol) is added to 260 mg of 55% sodium hydride in vaseline oil in 20 cm3 of DMF, then 2.41 g of [cis-[2-(2,4-dichlorophenyl)-2-(1H-imidazol-1-ylmethyl)-1,3-dioxolan-4-yl]methyl]4-methyl-benzenesulphonate is added at ambient temperature and stirring is carried out for 6 hours at 60° C. then for 12 hours at ambient temperature. The reaction medium is poured into ice-cooled water, extracted with dichloromethane, washed with 2N soda then with a saturated solution of NaCl, dried, filtered then evaporated under reduced pressure until a crude product is obtained which is purified by recrystallization from cyclohexane. 1.58 g of expected product is obtained. M.p.=160° C. Rf 0.15 Cyclohexane/ethyl acetate 5/5.

NMR CDCl$_3$ 300 MHz 3.49 (dd, 1H) and 3.94 (dd, 1H), 3.92 (dd) and 4.01 (dd) 2H: O—CH$_2$—CH—CH$_2$—O; 4.59 (m, 1H, O—CH$_2$—CH—CH$_2$—O); 4.46 and 4.55 (AB, 2H, N—CH$_2$—Cq); 6.80 (d, 1H, H10); 7.93 (d, 1H, H9); 9.30 (d) and 8.19 (bd) 2H H3 and H6; 7.57 (td) and 7.70 (td) 2H H4 and H5; 9.31; 7.50 (d, 1H, Ha); 7.63 (d, 1H, Hc); 7.31 (dd, 1H, Hb); 7.00 (bs, 2H, H'4 and H'5); 7.59 (bs, 1H, H'2); 10.20 (s, 1H, CHO). The H's correspond to the imidazole hydrogens.

Stage b) Formation of the amine: cis-4-[(2-(2,4-dichloro-phenyl)-2-(1H-imidazol-1-ylmethyl)-1,3-dioxolan-4-yl]methoxy]-N-methyl-1-naphthalenemethanamine Methylamine hydrochloride (1.33 g, 20 mmoles) then sodium cyanoborohydride (124 mg, 2 mmoles) are added to an aldehyde solution prepared in the previous stage (960 mg, 2 mmol) in 20 cm3 of methanol and 8 cm$^3$ of dichloromethane, and stirred for 12 hours at ambient temperature. The reaction medium is then evaporated under reduced pressure and the residue purified by chromatography on silica eluting with a CH$_2$Cl$_2$/MeOH mixture 9/1. 240 mg of expected product, 150 mg of expected partially salified product and 90 mg of a mixture of the two are obtained in several fractions. Rf 0.20 CH$_2$Cl$_2$/MeOH 90/10.

NMR CDCl$_3$ 300 MHz 3.12 (m, 2H) and 3.80 (m, 2H): O—CH$_2$—CH—CH$_2$—O; 4.40 (m, 1H, O—CH$_2$—CH—CH$_2$—O); 4.34 (AB, 2H, N—CH$_2$—Cq); 4.41 (AB, 2H, N—CH$_2$—Cq); 2.70 (s, 3H, N—CH$_3$); 7.46 (d, 1H, Ha); 7.28 (dd, 1H, Hb); 7.57 (d, 1H, Hc); 6.68 (bs, 1H); 6.82 (bs, 1H); 7.20 (bs, 1H): H of the imidazole; 7.54 (d, 1H), 6.27 (d, 1H)H10 and H9; 8.13 (d) and 7.50 (masked) and 7.64 (bt) and 7.99 (d) 4H: H3, H4, H5 and H6.

Example 1 cis-4-[[2-(2,4-dichlorophenyl)-2-(1H-imidazol-1-ylmethyl)-1,3-dioxolan-4-yl]methoxy]-N-methyl-N-(3-phenyl-2(E)-propenyl)-benzenemethanamine

1 drop of water is added to a suspension constituted by [cis-[2-(2,4-dichlorophenyl)-2-(1H-imidazol-1-ylmethyl)-1,3-dioxolan-4-yl]methyl] 4-methyl-benzenesulphonate (180 mg, 0.372 mmol) (prepared according to J. Med Chem. (1979) Vol 22, No. 8 1003–1008), P1 (104 mg, 0.410 mmol), tribenzylammonium chloride (TEBAC) (10.4 mg), isobutyl-methylcetone (MIBUC) (1.8 ml) and potassium carbonate (52 mg), and heated at 80–90° C. for 1 hour 15 then for 5 hours under reflux. [Cis-(2-(2,4-dichlorophenyl)-2-(1H-imidazol-1-ylmethyl)-1,3-dioxolan-4-yl]methyl]4-methyl-benzenesulphonate (78 mg, 0.161 mmol) is also added and reflux is maintained for 2 hours 30 minutes then finally a spatula tip of TEBAC and potassium carbonate are added and the reaction medium is maintained under reflux for 13 hours 30 minutes. Evaporation of the reaction medium is followed by chromatography on silica eluting with the CH$_2$Cl$_2$/MeOH mixture 98/2. Two fractions of 56 mg and 57 mg are obtained which are repurified in order to obtain 53 mg of expected product. Rf=0.40 CH$_2$Cl$_2$/MeOH 90/10.

NMR $^1$H (300 MHz CDCl$_3$) 2.23 (s, 3H, CH$_3$—N); 3.19 (bd, 2H, N—CH$_2$—CH═CH—); 6.31 (td, 1H, J=7, 16 Hz, N—CH$_2$—CH═CH—); 6.54 (bd, 1H, J=16 Hz, N—CH$_2$—CH═CH—); 3.33 (dd) and 3.75 (m) 2H, 3.75 (m) and 3.89 (dd) 2H: O—CH$_2$—CH—CH$_2$—O; 4.36 (m, 1H, O—CH$_2$—CH—CH$_2$—O); 7.26 (m, 1H, Hb); 3.51 (bs, 2H, N—CH$_2$—Cq) 4.40 and 4.51 (AB, 2H, Ph—CH$_2$—N); 6.78 and 7.25 (AA'BB', O—Ph); 6.99 (bd, 2H, H4 and H5); 7.52 (bs, 1H, H2); 7.58 (d, 1H, Hc); 7.47 (d, 1H, Ha); 7.39 (bd, 2H), 7.32 (bd, 2H), 7.26 (masked): aromatic H.

Example 2 cis-4-[[2-(2,4-dichlorophenyl)-2-[(1H-imidazol-1-ylmethyl)-1,3-dioxolan-4-yl]methoxy]-N-(3-phenyl-2(E)-propenyl)-4-chloro-benzenemethanamine

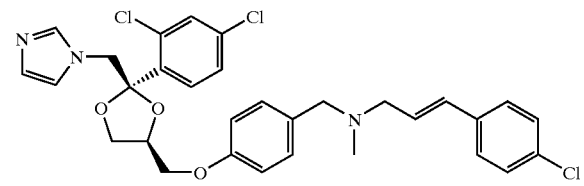

2 cm$^3$ of water, 42 mg of TPPTS (tris(3-sulphonatophenyl) phosphine tetrahydrate sodium salt, STREM CHEMICAL) and 18 mg of palladium II acetate are mixed for one hour at ambient temperature under a nitrogen atmosphere then a solution of the amine derivative P3 (312 mg, 0.7 mmole) and para-chloro-(E)-cinnamyl acetate (105 mg, 0.5 mmole in acetonitrile (2 cm3) is added. The reaction medium is stirred for 1 hour 30 minutes at 50° C., allowed to return to ambient temperature, water is added and extraction carried out several times with dichloromethane, followed by drying over MgSo4, filtering and evaporation under reduced pressure in order to obtain the expected crude product which is purified by chromatography on silica eluting with a CH$_2$Cl$_2$/MeOH mixture 90/10. 154 mg of expected purified product is obtained. Rf 0.15 CH$_2$Cl$_2$/MeOH 9/1.

NMR 1H (300 MHz CDCl$_3$) 2.32 (bs, 3H, CH$_3$—N); 3.30 (m, 2H, N—CH$_2$—CH═CH—); 6.32 (dt, 1H, J=16 and 7 Hz, N—CH$_2$—CH═CH—); 6.52 (d, 1H, J=16 Hz, N—CH$_2$—CH═CH—); 3.30 (m) and 3.75 (m) 2H, 3.75 (m) and 3.89 (dd) 2H: O—CH$_2$—CH—CH$_2$—O; 4.36 (m, 1H, O—CH$_2$—CH—CH$_2$—O); 3.64 (bs, 2H, Cq—CH$_2$—N); 6.81 and 7.31 (AA'BB', Ph—O); 7.47 (d, 1H, Ha); 7.25 (masked, 1H, Hb); 7.60 (d, 1H, Hc); 7.31 (AA'BB', Ph); 7.53 (bs, H, H2); 6.92 (bd, 2H, H4 and H5).

Example 3 cis-4-[[[4-[[2-(2,4-dichlorophenyl)-2-(1H-imidazol-1-ylmethyl)-1,3-dioxan-4-yl]methoxy]phenyl]methyl]methylamino]-1(E)-propenyl]-phenol

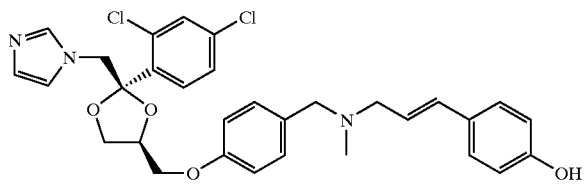

Stage a): cis-4-[[2-(2,4-dichlorophenyl)-2-(1H-imidazol-1-ylmethyl)-1,3-dioxolan-4-yl]methoxy]-N-[3-[4-[(2-methoxyethoxy)methoxy]phenyl]-2(E)-propenyl]-N-methyl-benzenemethanamine P4 (1.232 g, 0.0052 mol) is added to a solution of P3 (1.225 g, 0.0027 mol) in methanol (40 ml), the pH is adjusted to 6–7 by the addition of 100 µl of acetic acid then 95% NaBH$_3$CN (373 mg, 0.00564 mol). After reaction for 24 hours, evaporation is carried out under reduced pressure, and the residue obtained is taken up in dichloromethane (60 ml), washed, dried and again evaporated under reduced pressure until a dry extract is obtained, which is purified by chromatography on silica eluting with a dichloromethane/methanol mixture 95/5. 1.097 g of the expected purified product is obtained. Rf 0.47 dichloromethane/methanol 93/7.

NMR 300 MHz DMSO 2.45 (s, 3H, N—CH$_3$); 3.23 (s, 3H, CH$_3$—O—(CH$_2$)$_2$—O—CH$_2$—O); 3.47 (m, 2H) and 3.73 (m, 2H): CH$_3$—O—(CH$_2$)$_2$—O—CH$_2$—O; 5.25 (s, 2H, CH$_3$—O—(CH$_2$)$_2$—O—CH$_2$—O); 3.54 (bd, 2H, N—CH$_2$—CH=CH—Ph); 6.22 (td, 1H, J=7, 16 Hz, N—CH$_2$—CH=CH—Ph); 6.66 (bd, 1H, J=16 Hz, N—CH$_2$—CH=CH—Ph); 3.94 (1, 2H, Ph—CH$_2$—N); 3.69 (m) and 3.90 (dd) 2H, 3.68 to 3.84 (m, 2H): O—CH$_2$—CH—CH$_2$—O; 4.38 (m, 1H, O—CH$_2$—CH—CH$_2$—O); 4.54 (s, 2H, N—CH$_2$-Cq); 6.94 and 7.38 AA'BB', 7.01 and 7.42 AA'BB': Ph—O; 6.83 (bs) and 7.00 (m) 2H H4 and H5; 7.51 (bs, 1H, H2); 7.63 (d, 1H, Ha); 7.57 (d, 1H, Hc); 7.42 (m, 1H, Hb).

Stage b) Deprotection: cis-4-[3-[[[4-[[2-(2,4-dichlorophenyl)-2-[1H-imidazol-1-ylmethyl]-1,3-dioxan-4-yl]methoxy]phenyl]methyl]methylamino]-1(E)-propenyl]-phenol The mixture constituted by (I) (1.028 g, 1.5 mmoles) in 20 ml of dichloromethane and 20 ml of TFA (trifluoroacetic acid) is stirred for 3 hours at 0° C., then evaporated under reduced pressure until a residue is obtained which is taken up in dichloromethane (60 ml). The organic phase is washed, dried and evaporated under reduced pressure until a dry extract is obtained which is purified by chromatography on silica eluting with a dichloromethane/ethanol mixture 93/7. 425 mg of the expected purified product is obtained. Rf 0.16 dichloromethane/methanol 93/7.

NMR 300 MHz CDCl$_3$ 2.38 (s, 3H, N—CH$_3$); 3.69 (1, 2H, N—CH$_2$—Ph); 3.42 (dd) and 3.69 (masked) 2H, 3.28 (masked) and 3.75 (dd) 2H: O—CH$_2$—CH—CH$_2$—O; 4.35 (m, 1H, O—CH$_2$—CH—CH$_2$—O); 3.30 (m, 2H, N—CH$_2$—CH=CH—Ph); 5.90 (td, 1H, J=7.5; 16 Hz, N—CH$_2$—CH=CH—Ph); 6.40 (d, 1H, J=16 Hz, N—CH$_2$—CH=CH—Ph); 4.52 and 4.43 (AB, 2H, N—CH$_2$-Cq); 6.76 and 7.26 (AA'BB'), 6.80 and 7.09 (AA'BB') 8H, 7.63 (bs, 1H, H2); 7.64 (d, 1H, Hc); 7.49 (d, 1H, Ha); 7.29 (masked Hb); 7.03 (m, 2H, H4 and H5).

Example 4 cis-4-[[2-(2,4-dichlorophenyl)-2-(1H-imidazol-1-ylmethyl)-1,3-dioxolan-4-yl]methoxy]-N-(3-phenyl-2(E)-propenyl)-benzenemethanamine

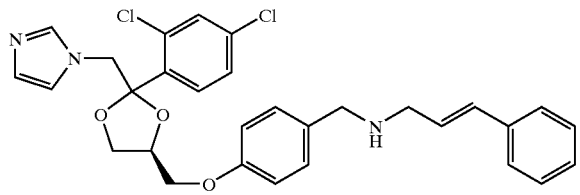

Sodium cyanoborohydride (62 mg, 169 mmol) is added to a solution of P2 (433 mg, 1 mmole) and 3-phenylallylamine hydrochloride (ref Sigma)(200 mg, 1.2 mmole) in 12 cm3 of methanol and stirred overnight at ambient temperature. Following evaporation under reduced pressure, the oily residue is taken up in ethyl acetate, washed with a 2N soda solution, dried over MgSO$_4$, and taken to dryness under vacuum. 592 mg of crude product is obtained which is purified by chromatography on silica eluting with a CH$_2$Cl$_2$/MeOH mixture 9/1 to which 1% of water has been added. 225 mg of expected pure product is obtained. Rf 0.20 CH$_2$Cl$_2$/MeOH 90/10+1% water.

3.33 (dd) and 3.76 (m) 2H, 3.75 (m) and 3.84 (dd) 2H: O—CH$_2$—CH—CH$_2$—O; 4.36 (m, 1H, O—CH$_2$—CH—CH$_2$—O); 4.40 and 4.51 (AB, 2H, N—CH$_2$—Cq); 3.43 (bd, 2H, N—CH$_2$—CH=CH—Ph); 6.32 (td, 1H J=16 and 6.5 Hz, N—CH$_2$—CH=CH—Ph); 6.55 (bd, 1H, J=16 Hz, N—CH$_2$—CH=CH—Ph); 3.78 (bs, 2H, N—CH$_2$—Ph); 6.79 and 7.26 (AA'BB', 4H, Ph—O); 6.98 (m, 2H, H4 and H5); 7.47 (d, 1H, Ha); 7.58 (d, 1H, Hc); 7.38 (bd, 2H, H ortho); 7.31 (bt, 2H, H meta); 7.23 (masked, 2H, H para and Hb); 7.51 (bs, 1H, H2).

Example 5

Mono[cis-4-[3-[[[4-[[2-(2,4-dichlorophenyl)-2-(1H-imidazol-1-ylmethyl)-1,3-dioxan-4-yl]methoxy]phenyl]methyl]methylamino]-1(E)-propenyl]phenyl] phosphate(trifluoroacetate salt)

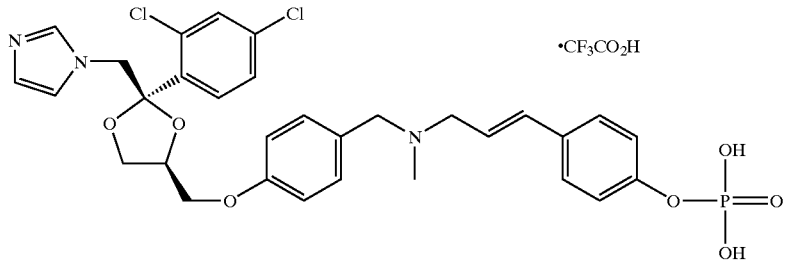

Stage a) Phosphorylation: [cis-4-[3-([[4-[[2-(2,4-dichlorophenyl)-2-(1H-imidazol-1-ylmethyl)-1,3-dioxan-4-yl]methoxy]phenyl]methyl]methylamino]-1(E)-propenyl]phenyl]and bis(phenylmethyl) phosphate 665 μl of $CCl_4$, 17 mg of DMAP, 480 μl of diisopropylethylamine then dropwise dibenzylphosphite (460 μl, 2.08 mmol) are added to absolution of (I) (400 mg, 0.689 mmol) in dichloromethane (12 ml) cooled down to −5° C. After stirring for 3 hours at 0° C. the reaction medium is then washed with 30 ml of $NaH_2PO_4$ (1M) then 10 ml of a saturated aqueous solution of NaCl. The organic phases are then dried then evaporated under reduced pressure until a dry extract is obtained which is purified by filtration on silica eluting with a dichloromethane/MeOH mixture 95/5. 234 mg of expected product is obtained. Rf 0.42 dichloromethane/methanol 93/7.

Stage b) Deprotection: mono[cis-4-[3-[[[4-[[2-(2,4-dichlorophenyl)-2-(1H-imidazol-1-ylmethyl)-1,3-dioxan-4-yl]methoxy]phenyl]methyl]methylamino]-1(E)-propenyl]phenyl]phosphate (trifluoroacetate salt)

The mixture constituted by (I) (234 mg) in 5 ml of dichloromethane and 5 ml of TFA (trifluoroacetic acid) is stirred for 5 hours at ambient temperature, then evaporated under reduced pressure until a dry extract is obtained which is purified by HPLC on Kromasil C18 10μ eluting with an acetonitrile/water mixture 40/60 (+0.03% of TFA). 119 mg of the expected purified product is obtained. Rf 3.24 acetonitrile/water 40/60.

NMR 300 MHz DMSO 2.65 (s, 3H, N—C$\underline{H}_3$); 4.28 (bs, 2H, N—C$\underline{H}_2$—Ph); 3.85 (bd, 2H, N—C$\underline{H}_2$—CH═CH—Ph); 6.29 (td, 1H, J=6.5; 16 Hz, N—CH$_2$—C$\underline{H}$═CH—Ph); 6.80 (bd, 1H, J=16 Hz, N—CH$_2$—CH═C$\underline{H}$—Ph); 4.76 and 4.83 (AB, 2H, N—C$\underline{H}_2$—Cq); 9.00 (bs, 1H, H2); 3.68 (dd) and 3.43 (dd) 2H, 3.71 (dd) and 3.87 (dd) 2H: O—C$\underline{H}_2$—CH—C$\underline{H}_2$—O; 4.41 (m, 1H, O—CH$_2$—C$\underline{H}$—CH$_2$—O); 6.96 and 7.46 AA'BB', 7.18 and 7.49 AA'BB' (8H); 7.54 (m, 3H, Hb, H4 and H5); 7.65 (d, 1H, Hc); 7.74 (d, 1H, Ha); 9.97 (bs, 1H mobile)

Example 6 cis-4-[[2-(2,4-dichlorophenyl)-2-(1H-imidazol-1-ylmethyl)-1,3-dioxolan-4-yl]methoxy]-N-methyl-N-(3-phenyl-2(E)-propenyl)-1-naphthalenemethanamine Sodium cyanoborohydride (30 mg) is added to a mixture constituted by P5 (240 mg, 0.48 mmole) and trans-cinnamaldehyde (120 μl, 0.96 mmole) in methanol (10 cm$^3$) the pH of which is equal to approximately 6 by the addition of acetic acid (15 μl), and left to react for 12 hours under stirring, followed by evaporation under reduced pressure and purification by chromatography on silica eluting with a $CH_2Cl_2$/MeOH 93/7 mixture in order to obtain 104 mg of expected product. Rf 0.20 $CH_2Cl_2$/MeOH 93/7.

NMR CDCl$_3$ 300 MHz 2.28 (s, 3H, N—C$\underline{H}_3$); 3.30 (bd, 2H, N—C$\underline{H}_2$—CH═CH—Ph); 6.38 (bt, 1H, J=7, 16 Hz, N—CH$_2$—C$\underline{H}$═CH—Ph); 6.58 (bd, 1H J=16 Hz, N—CH$_2$—CH═C$\underline{H}$—Ph); 4.45 and 4.54 (AB, 2H, N—C$\underline{H}_2$—Cq); 3.92 (bs, 2H, N—CH$_2$—Ph); 3.54 (dd) and 3.96 (dd) 2H, 3.88 (dd) and 3.98 (dd) 2H: O—C$\underline{H}_2$—CH—C$\underline{H}_2$—O; 4.54 (m, 1H, O—CH$_2$—C$\underline{H}$—CH$_2$—O); 8.18 (bd, 1H) and 8.23 (bd, 1H): H3 and H6; 7.49 (d, 1H, Ha); 7.60 (d, 1H, Hc); 6.65 (bd, 1H, H10); 7.37 (m, 1H, H9); 7.00 (bs, 2H), 7.16 to 7.58 (m, 9H): Hb, H2', H4', H5', H3, H6, phenyl H.

Example 7 cis-4-[[2-(2,4-dichlorophenyl)-2-(1H-imidazol-1-ylmethyl)-1,3-dioxolan-4-yl]methoxy]-N-[3-[4-(2-hydroxy-ethoxy)phenyl]-2(E)-propenyl]-N-methyl-benzenemethanamine

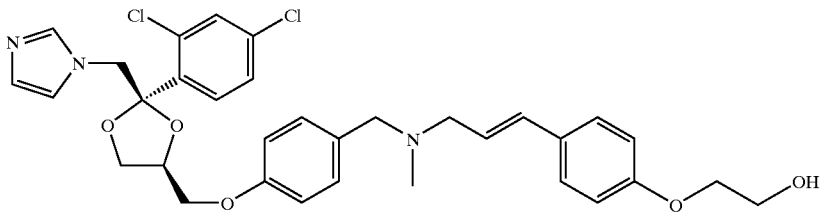

The mixture constituted by the phenol prepared in Example 3 (89 mg, 0.15 mmol), K₂CO₃ (23 mg, 0.16 mmol) and 1,3-dioxolan-2-one (68 mg, 0.77 mmol) in 2 ml of DMF is stirred overnight at 80° C., the reaction mixture is diluted with 10 ml of ethyl acetate. After washing and drying, evaporation is carried out under reduced pressure in order to obtain 110 mg of crude product which is purified by chromatography on silica eluting with a CH₂Cl₂/MeOH mixture 93/7. 32 mg of expected pure product is obtained. Rf 0.30 CH₂Cl₂/MeOH 93.00/7.00.

3.33 (dd) and 3.76 (m) 2H, 3.75 (m) and 3.84 (dd) 2H: O—CH₂—CH—CH₂—O; 4.37 (m, 1H, O—CH₂—CH—CH₂—O); 3.97 (m, 2H), 4.07 (m, 2H): O—(CH₂)₂—O; 4.41 and 4.52 (AB, 2H, N—CH₂-Cq); 6.97 (m, 2H, H4 and H5); 3.24 (bs, 2H, N—CH₂—CH=CH—Ph); 6.20 (td, 1H J=16 and 7 Hz, N—CH₂—CH=CH—Ph); 6.51 (bd, 1H, J=16 Hz, N—CH₂—CH=CH—Ph); 2.28 (bs, 3H, N—CH₃); 3.57 (bs, 2H, Ph—CH₂—N); 6.79 and 7.28 (AA'BB'), 6.87 and 7.33 (AA'BB'): 8H, 7.26 (masked, 1H, Hb); 7.59 (d, 1H, Hc); 7.47 (d, 1H, Ha); 7.51 (bs, 1H, H2).

Example 8

Cis-N-(2-aminoethyl)-4-[2-(2,4-dichlorophenyl)-2-(1H-imidazol-1-ylmethyl)-1,3-dioxolan-4-yl]methoxy]-N-(3-phenyl-2(E)-propenyl)-benzenemethanamine trifluoroacetate

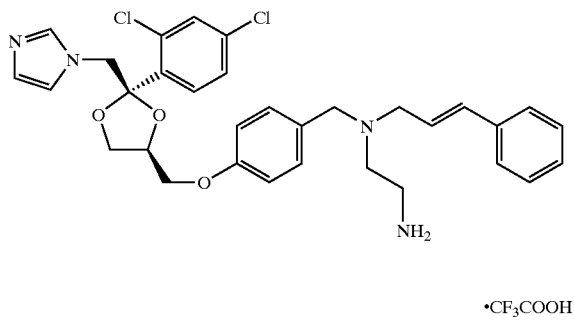

Stage a) 1,1-dimethylethyl cis-[2-[[[4-[[2-(2,4-dichlorophenyl)-2-(1H-imidazol-1-ylmethyl)-1,3-dioxolan-4-yl]methoxy]phenyl]methyl]amino]ethyl]-carbamate (P6)

N-Boc-ethylenediamine (400 µl) is added to a solution of P2 (1 g, 2.30 mmol) in MeOH (30 ml), the pH is adjusted to approximately 6 by adding acetic acid (200 µl) then after 15 minutes, NaBH₃CN (227 mg) is added and stirring is carried out for 18 hours at ambient temperature. The reaction medium is then filtered and brought to dryness. The residue is taken up in dichloromethane, the organic phase is washed, dried then evaporated under reduced pressure in order to obtain 1.3 g of crude product which is purified by chromatography eluting with a CH₂Cl₂/MeOH mixture (9/1). 875 mg of expected product is obtained. Rf 0.16 CH₂Cl₂/MeOH 90/10.

NMR CDCl₃ 300 MHz 1.43 (s, 9H, O—C(CH₃)₃); 3.42 (dd) and 3.66 (dd) 2H, 3.78 (dd) and 3.89 (dd) 2H: O—CH₂—CH—CH₂—O; 4.37 (m, 1H, O—CH₂—CH—CH₂—O); 3.00 (m, 1H, Ph—CH₂—NH—CH₂—CH₂—NH); 3.00 (bt, 2H); 3.94 (bs, 2H, Ph—CH₂—NH—CH₂—CH₂—NHCO); 3.35 (m, 2H, Ph—CH₂—NH—CH₂—CH₂—NHCO); 5.42 (bt, 1H, Ph—CH₂—NH—CH₂—CH₂—NHCO); 4.41 and 4.48 (AB, 2H, N—CH₂-Cq); 6.80 and 7.35 (AA'BB' 4H, O—Ph); 7.28 (m, 1H, Hb); 7.47 (d, 1H, Ha); 7.58 (d, 1Hc); 7.46 (masked, 1H, H2); 6.93 (bs, 2H, H4 and H5).

Stage b) 1,1-dimethylethyl cis-[2-[[[4-[[2-(2,4-dichlorophenyl)-2-(1H-imidazol-1-ylmethyl)-1,3-dioxolan-4-yl]methoxy]phenyl]methyl](3-phenyl-2(E)-propenyl)amino]ethyl]-carbamate After 15 minutes, whilst maintaining a pH of the order of 6, NaBH₃CN (54 mg) is added to a mixture constituted by (I) (287 mg, 0.498 mmol) and trans-cinnamaldehyde (69.2 µl) in methanol (6 ml) and reacted for 1 hour 10 minutes under stirring, followed by evaporation under reduced pressure and purification by chromatography on silica eluting with a CH₂Cl₂/MeOH mixture 95/5 in order to obtain 135 mg of expected product. Rf 0.49 CH₂Cl₂/MeOH 95/5.

NMR CDCl₃ 300 MHz 1.43 (s, 9H, O—C(CH₃)₃); 2.62 (bt, 2H, Ph—CH₂—NH—CH₂—CH₂—NHCO); 3.24 (bt, 2H, Ph—CH₂—NH—CH₂—CH₂—NHCO); 4.99 (bs, 1H, Ph—CH₂—NH—CH₂—CH₂—NHCO); 3.34 (dd) and 3.76 (dd) 2H, 3.75 (dd) and 3.90 (dd) 2H: O—CH₂—CH—CH₂—O; 4.37 (m, 1H, O—CH₂—CH—CH₂—O); 4.41 and 4.53 (AB, 2H, N—CH₂—Cq); 3.60 (bs, 2H, Ph—CH₂—N); 3.27 (masked, 2H, N—CH₂—CH=CH—Ph); 6.27 (td, 1H, J=7, 16 Hz, N—CH₂—CH=CH—Ph); 6.52 (bd, 1H, J=16 Hz, N—CH₂—CH=CH—Ph); 6.79 and 7.25 (AA'BB' 4H, Ph—O); 6.99 (m, 2H, H4 and H5); 7.58 (m, 1H, Hc); 7.52 (bs, 1H, H2); 7.47 (d, 1H, Ha); 7.26 (m, 1H, Hb); 7.20 to 7.40 (m, 5H Ph).

Stage c) Cis-N-(2-aminoethyl)-4-[[2-(2,4-dichlorophenyl)-2-(1H-imidazol-1-ylmethyl)-1,3-dioxolan-4-yl]methoxy]-N-(3-henyl-2(E)-propenyl)-benzenemethanamine trifluoroacetate Trifluoroacetic acid (3.4 ml) is added to a solution of (I) (130 mg, 0.178 mmol) in dichloromethane (1.4 ml), at 0–5° C., stirred for 20 minutes at this temperature then left to warm up to ambient temperature for 2 hours, followed by evaporation under reduced pressure. The residue is taken up in dichloromethane, washed, and dried in order to obtain 115 mg of crude product which is purified by HPCL on Kramasil $C_{18}$ eluting with an acetonitrile/water mixture 60/40 to which 0.03% of TFA is added. 79 mg of expected pure product is obtained. Rf 3.68 acetonitrile/water 60/40 to which +0.03% of TFA.

NMR $CDCl_3$ 300 MHz 4.57 and 4.67 (AB, 2H, N—$CH_2$—Cq); 4.00 (b, 2H, N—$CH_2$—CH=CH—Ph); 6.39 (1, 1H, J=7, 16 Hz, N—$CH_2$—C$\underline{H}$=CH—Ph); 6.85 (bd, 1H, J=16 Hz, N—$CH_2$—CH=C$\underline{H}$—Ph); 7.33 (masked, 1H, Hb); 7.50 (d, 1H, Ha); 7.66 (dd, 1H, Hc); 6.76 and 7.37 (AA'BB' 4H, Ph—O); 3.88 (m) and 3.50 (m) and 3.47 (m) 4H: O—C$\underline{H}_2$—CH—C$\underline{H}_2$—O; 4.40 (bs, 1H, O—$CH_2$—C$\underline{H}$—$CH_2$—O); 3.41 (b) and 3.62 (1) 4H: N—($CH_2$)$_2$—$NH_2$; 4.19 (b, 2H, N—$CH_2$—Ph); 8.66 (s, 1H, H2); 7.19, (bs) and 7.37 (bs) 2H: H4 and H5; 7.45 (m, 2H) and 7.36 (m, 3H): phenyl H.

Example 9 cis-N-(2-aminoethyl)-N-[3-(4-chlorophenyl)-2(E)-propenyl]-4-[[2-(2,4-dichlorophenyl)-2-(1H-imidazol-1-ylmethyl)-1,3-dioxolan-4-yl]methoxy]-benzenemethanamine

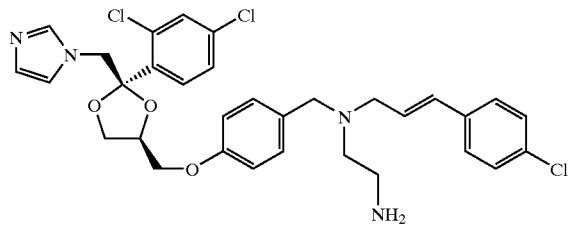

Stage a) 1,1-dimethylethyl cis-[2-[[[[3-(4-chlorophenyl)-2(E)-propenyl]-4-[2-(2,4-dichlorophenyl)-2-(1H-imidazol-1-ylmethyl)-1,3-dioxolan-4-yl]methoxy]phenyl]methyl]amino]ethyl]-carbamate The mixture constituted by palladium (II) acetate (7 mg) and sodium tris(3-sulphonatophenyl)phosphine tetrahydrate (tppts, Strem Chemical) (52.6 mg) in demineralized water (2 ml) is stirred at ambient temperature for 1 hour, then a solution of para-chloro-(E)-cinnamyl acetate (130 mg, 0.617 mol) and P6 (500 mg) in acetonitrile (2 ml) is added. After stirring for 2 hours at 50° C. the acetonitrile is evaporated off and the remaining aqueous phase is extracted with dichloromethane. The organic phase is then dried, filtered and evaporated under reduced pressure until a dry extract is obtained ((650 mg) which is purified by chromatography on silica eluting with a $CH_2Cl_2$/MeOH mixture (95/5) then (98/2). 134 mg of expected product is obtained. Rf 0.63 $CH_2Cl_2$/MeOH (90/10).

NMR ($CDCl_3$) 300 MHz 1.43 (s, 9H, OC($CH_3$)$_3$); 2.62 (bs, 2H, N—$CH_2$—$CH_2$—NH); 3.24 (b, 2H, N—$CH_2$—C$\underline{H}_2$—NH); 3.26 (m, 2H, N—C$\underline{H}_2$—CH=CH—Ph); 6.23 (td, 1H, J=6.516 Hz, N—$CH_2$—C$\underline{H}$=CH—Ph); 6.47 (bd, 1H, J=16 Hz, N—$CH_2$—CH=C$\underline{H}$—Ph); 3.31 (dd) and 3.74 (dd) 2H, 3.74 (dd) and 3.89 (dd) 2H: O—C$\underline{H}_2$—CH—C$\underline{H}_2$—O; 4.36 (m, 1H, O—$CH_2$—C$\underline{H}$—$CH_2$—O); 4.41 and 4.52 (AB, 2H, N—$CH_2$—Cq); 3.60 (bs, 2H, Ph—C$\underline{H}_2$—N); 4.97 (bs, 1H, mobile H); 6.78 and 7.24 (AA'BB', 4H, Ph—O); 7.29 (m, 4H, phenyl H); 7.27 (m, 1H, Hb); 7.59 (d, 1H, Hc); 7.47 (d, b, Ha); 6.99 (m, 2H, H4 and H5); 7.52 (bs, 1H, H2).

Stage b) Deprotection: cis-N-(2-aminoethyl)-N-[3-(4-chlorophenyl)-2(E)-propenyl]-4-[[2-(2,4-dichlorophenyl)-2-(1H— imidazol-1-ylmethyl)-1,3-dioxolan-4-yl]methoxy]-benzenemethanamine Trifluoroacetic acid (3.4 ml) is added, at 0° C.–5° C., to a solution of the derivative prepared in the previous stage (130 mg, 0.178 mmol) in dichloromethane (1.4 ml), followed by stirring for 20 minutes at this temperature then the medium is left to warm up to ambient temperature for 2 hours, then evaporated under reduced pressure, taken up in dichloromethane, washed with 2N soda, then with a saturated solution of NaCl. The organic phase is dried, filtered, and brought to dryness. 108 mg of expected product is obtained. Rf 0.09 $CH_2Cl_2$/MeOH (85/15).

NMR ($CDCl_3$) 300 MHz 2.78 (m, 2H, N—C$\underline{H}_2$—$CH_2$—N); 2.54 (m, 2H, N—$CH_2$—C$\underline{H}_2$—N); 3.39 (dd) and 3.60 (dd) 2H, 3.76 (dd) and 3.87 (dd) 2H: O—C$\underline{H}_2$—CH—C$\underline{H}_2$—O; 4.37 (m, 1H, O—$CH_2$—C$\underline{H}$—$CH_2$—O); 4.39 and 4.50 (AB, 2H, N—$CH_2$—Cq); 3.27 (d, 2H, N—C$\underline{H}_2$—CH=CH—Ph); 6.26 (td, 1H J=7, 16 Hz, N—$CH_2$—C$\underline{H}$=CH—Ph); 6.48 (bd, 1H, J=16 Hz, N—$CH_2$—CH=C$\underline{H}$—Ph); 3.57 (bs, 2H, Ph—C$\underline{H}_2$—N); 6.77 and 7.23 (AA'BB', 4H, Ph—O); 6.96 (m, 2H, H4 and H5); 7.29 (m, 4H, phenyl H); 7.47 (d, 1H, Ha); 7.43 (bs, 1H, H2); 7.60 (d, 1H, Hc); 7.27 (m, b, Hb).

Example 10 cis-2-[[[4-[[2-(2,4-dichlorophenyl)-2-(1H-imidazol-1-ylmethyl)-1,3-dioxolan-4-yl]methoxy]phenyl]methyl](3-phenyl-2(E)-propenyl)amino]-ethanol

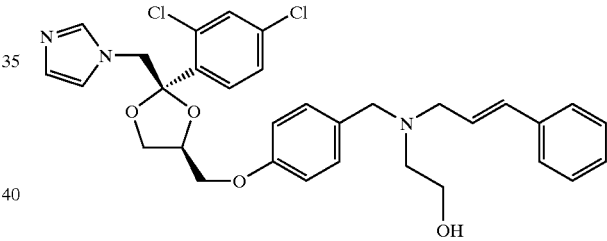

Stage a) Formation of the alcohol: cis-2-[[[4-[[2-(2,4-dichlorophenyl)-2-(1H-imidazol-1-ylmethyl)-1,3-dioxolan-4-yl]methoxy]phenyl]methyl]amino]-ethanol P2 (1 g, 2.30 mmol) and ethanolamine (153 μl) in 30 ml of methanol are mixed together, acetic acid (200 μl), adjusting the pH to 5.5 then after 15 minutes $NaBH_3CN$ (174 mg) is added. After stirring for 1 hour 30 minutes, and evaporation under reduced pressure, the residue is taken up in dichloromethane, the organic phase is washed, dried and taken to dryness in order to obtain 1.31 g of crude product which is purified by chromatography on silica eluting with a $CH_2Cl_2$/MeOH/water mixture 90/10/0.01. 818 mg of expected product is obtained. Rf 0.09 $CH_2Cl_2$/MeOH (85/15).

3.07 (bs, 2H, N—C$\underline{H}_2$—$CH_2$—O); 3.81 (m, 2H, N—$CH_2$—C$\underline{H}_2$—O); 3.39 (dd) and 3.53 (dd) 2H and 3.83 (m, 2H): O—C$\underline{H}_2$—CH—C$\underline{H}_2$—O; 4.38 (m, 1H, O—$CH_2$—C$\underline{H}$—$CH_2$—O); 4.09 (bs, 2H, Ph—$CH_2$—N); 4.41 and 4.50 (AB, 2H, N—$CH_2$—Cq); 6.79 and 7.41 (AA'BB' 4H, Ph—O); 6.92 (bs) and 6.97 (bs, 2H, H4 and H5); 7.54 (bs, 1H, H2); 7.29 (dd, 1H, Hb); 7.47 (d, 1H, Ha); 7.62 (d, 1H, Hc); 6.24 (bs, 4H, mobile H).

Stage b) Cis-2-[[[4-[[2-(2,4-dichlorophenyl)-2-(1H-imidazol-1-ylmethyl)-1,3-dioxolan-4-yl]methoxy]phenyl]methyl](3-phenyl-2(E)-propenyl)amino]-ethanol After 15 minutes, maintaining a pH of the order of 5.5, NaBH₃CN (59 mg) is added to a mixture constituted by the alcohol prepared in the previous stage (300 mg, 0.627 mmol) and trans-cinnamaldehyde (111 µl) in methanol (6 ml) and reacted for 3 hours 45 minutes under stirring, followed by evaporation under reduced pressure and purification by chromatography on silica eluting with a CH₂Cl₂/MeOH 95/5 mixture in order to obtain 127 mg of expected product. Rf 0.78 CH₂Cl₂/MeOH 90/10.

NMR CDCl₃ 300 MHz 3.23 (bd, 2H, N—C$\underline{H}$₂—CH═CH—Ph); 6.33 (td, 1H, J=6.5, 16 Hz, N—CH₂—C$\underline{H}$═CH—Ph); 6.55 (bd, 1H, J=16 Hz, N—CH₂—CH═C$\underline{H}$—Ph); 2.53 (masked, 2H, N—C$\underline{H}$₂—CH₂—OH); 3.49 (b, 2H, N—CH₂—C$\underline{H}$₂—OH); 4.38 (m, 1H, N—CH₂—CH₂—O$\underline{H}$); 3.58 (m) and 3.69 (m) 2H, 3.68 (m) and 3.88 (dd) 2H: O—C$\underline{H}$₂—CH—C$\underline{H}$₂—O; 4.38 (m, 1H, O—CH₂—C$\underline{H}$—CH₂—O); 3.32 (bs, 2H, N—C$\underline{H}$₂—Ph); 4.51 and 4.56 (AB, 2H, N—C$\underline{H}$₂—Cq); 7.68 (d, 1H, Ha); 7.58 (dd, 1H, Hc); 7.46 (m, 1H, Hb); 6.81 (bs) and 7.01 (bs) 2H H4 and H5; 7.46 (bs, 1H, H2); 6.84 and 7.26 (AA'BB' 4H, Ph—O); 7.22 (bt, 1H, H in para position of the phenyl); 7.32 (bt, 2H, H meta position of the phenyl); 7.43 (bd, 2H, H in ortho position of the phenyl).

In a Manner Similar to the Previous Examples, the Following Products were Prepared:

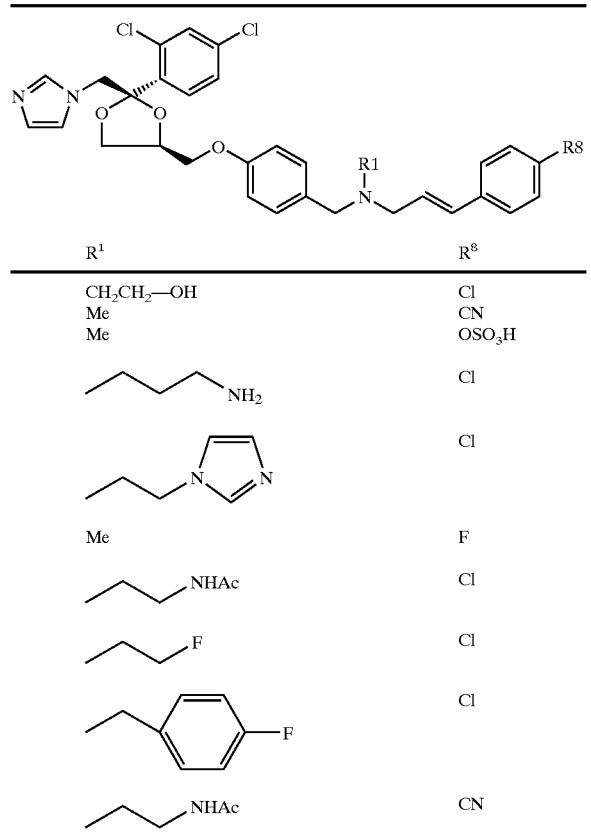

| R¹ | R⁸ |
|---|---|
| CH₂CH₂—OH | Cl |
| Me | CN |
| Me | OSO₃H |
| ~~~NH₂ | Cl |
| ~~N(imidazole) | Cl |
| Me | F |
| ~~~NHAc | Cl |
| ~~~F | Cl |
| ~~-Ph-F | Cl |
| ~~~NHAc | CN |

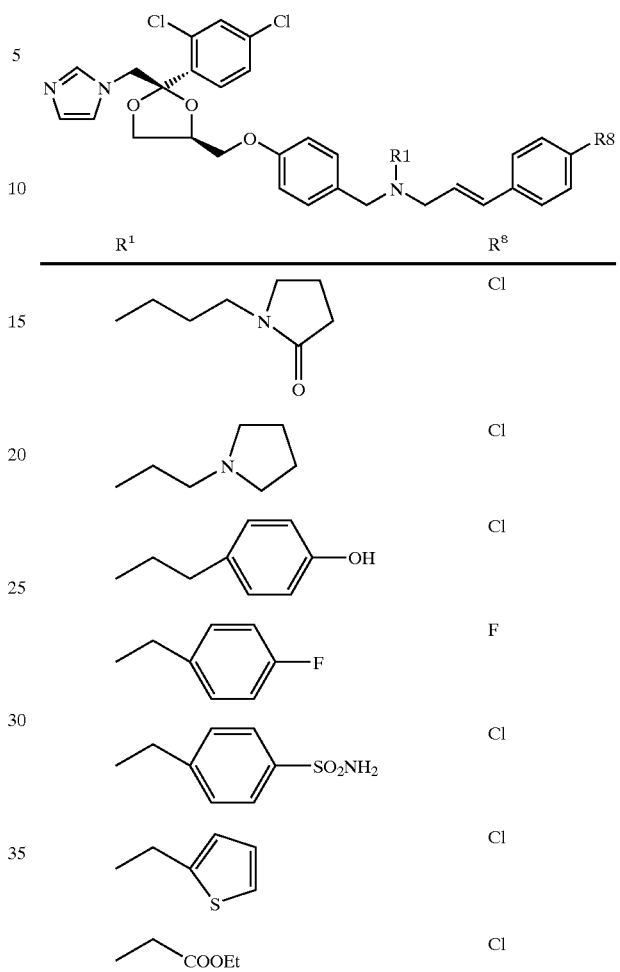

| R¹ | R⁸ |
|---|---|
| ~~~N(pyrrolidinone) | Cl |
| ~~~N(pyrrolidine) | Cl |
| ~~~-Ph-OH | Cl |
| ~~-Ph-F | F |
| ~~-Ph-SO₂NH₂ | Cl |
| ~~-thiophene | Cl |
| ~~~COOEt | Cl |

Pharmaceutical Compositions

Compounds were prepared, containing

| Example 1 Product | 50 mg |
|---|---|
| Excipient q.s.f. | 1 g |

Detail of the excipient: starch, talc, magnesium stearate.

Biological Activity

1) Antifungal Activity of the Compounds According to the Invention.

Female mice weighing from 18 to 22 g were used. A quantity of *Candida albicans* 44858 was administered into the tail vein at a rate of 10⁶CFU per mouse (CFU: colony forming unit). The mice are separated into 5 groups of 5 mice and treated as follows:

One hour after the infection

Group 1: the mice are treated with the product P 25 mg/kg by oral route

Group 2: the mice are treated with the product P by intraperitoneal route at a rate of 25 mg/kg Group 3: the mice are treated with fluconazole (25 mg/kg by oral route).

Group 4: the mice are treated with fluconazole (25 mg/kg by intraperitoneal route).

Group 5: the mice receive no antifungal treatment.

Over a period of 22 days, the dead mice are counted.

2) Minimum Inhibitory Concentration (MIC)

*Candida albicans* cells are prepared as indicated in Journal of Antimicrobial Chemotherapy 38, 579–587, washed 3 times with a 0.1 M phosphate solution and used immediately in order to determine the minimum inhibitory concentration (MIC).

The MICs are determined by the modification of a microtiter plate according to the standard method of the Comite National des standards cliniques de laboratoire.

RPMI-1640 is used as medium, and L-glutamine buffered to pH7 with a 0.15 M MOPS (3-[N-morpholino]propane sulphonic acid) solution. *Candida albicans* cells ($1.5 \times 10^3$ cells/ml) are added to the wells of a 96-well plate containing RPMI-1640 and the dilutions of antifungal agent. The results were read 48 hours after incubation at 35° C. and the MIC or minimum inhibitory concentration which inhibits the growth of *Candida albicans* cells was determined.

Minimum Fungicidal Concentration

After the MIC reading at 48 hours, the plates are shaken and 10 μL of aliquot is removed from the wells, and placed on rectangular disks containing dextrose agar. The plates are incubated for 48 hours at 35° C.; The minimum fungicidal concentration is the concentration of the antifungal agent at which the number of colony forming units is zero.

Conclusion

The compounds according to the invention described in the examples 1 to 10 show an activity at <100 μg/ml in the mic test.

What is claimed is:

1. A compound of the formula (I):

(I)

wherein

X is nitrogen or CH;

$Ar^1$ is a carbocyclic or heterocyclic aryl, non-substituted or substituted by one or more $R^2$, $R^3$ or $R^4$;

$Ar^2$ is phenylene or naphthalene, non-substituted or substituted by one or more $R^5$, $R^6$ or $R^7$;

$Ar^3$ is a carbocyclic or heterocyclic aryl, non-substituted or substituted by one or more $R^8$, $R^9$ or $R^{10}$;

A is ($C_1$–$C_4$)-alkylene or C(O);

B is ($C_1$–$C_4$)-alkylene-CH=CH— or ($C_1$–$C_4$)-alkylene-cyclopropylene, said cyclopropylene or —CH=CH— is optionally substituted by $R^2$ or $R^3$;

$R^1$ is hydrogen, —$SO_3H$ or ($C_1$–$C_6$)alkyl, non-substituted or substituted by $R^2$; and wherein $R^2$, $R^3$, $R^4$, $R^5$, $R^6$, $R^7$, $R^8$, $R^9$ or $R^{10}$, are the same or different and are independently selected from the group consisting of; fluorine, chlorine, bromine, cyano, mono- bi- or trihalogeno($C_1$–$C_8$)alkyl, mono- bi- or trihalogeno($C_1$–$C_8$)-alkyloxy, hydroxy, nitro, carboxyl, formyl, —$SO_3H$, —$OSO_3H$, $(R^{11}O)_2P(O)$—, $(R^{11}O)_2P(O)$—O—, amino, ($C_1$–$C_8$)-alkylamino, di(($C_1$–$C_8$)alkyl)amino, ($C_5$–$C_{14}$)-aryl-($C_1$–$C_6$)-alkylenamino or ($C_5$–$C_{14}$)-arylamino, ($C_1$–$C_8$)-alkyl, ($C_5$–$C_{14}$)aryl, a heterocycle optionally substituted by oxo, ($C_5$–$C_{14}$) aryl-($C_1$–$C_6$)alkyl, amino-($C_1$–$C_6$)-alkyl, ($C_1$–$C_8$)-alkylamino-($C_1$–$C_6$)-alkyl, di-(($C_1$–$C_8$)alkyl)amino-($C_1$–$C_6$)-alkyl, hydroxy-($C_1$–$C_6$)alkyl, ($C_1$–$C_6$)-alkyloxy-($C_1$–$C_6$)-alkyl, ($C_1$–$C_8$)-alkyloxy optionally interrupted by one or more oxygen atoms, ($C_5$–$C_{14}$)-aryl-($C_1$–$C_6$)-alkylenoxy, ($C_5$–$C_{14}$)-aryloxy, hydroxy-($C_1$–$C_6$)alkylenoxy, ($C_1$–$C_6$)-alkyloxy-($C_1$–$C_6$) alkylenoxy, amino-($C_1$–$C_6$)-alkylenoxy, ($C_1$–$C_6$)-alkylamino-($C_1$–$C_6$)-alkylenoxy, di(($C_1$–$C_8$)-alkyl) amino-($C_1$–$C_6$)-alkylenoxy, methylenedioxy, (C—$C_6$)-alkyloxycarbonyl, ($C_1$–$C_6$)-alkylcarbonyl, ($C_5$–$C_{14}$) aryl-($C_1$–$C_6$)-alkylenecarbonyl, ($C_5$–$C_{14}$)-arylcarbonyl, ($C_1$–$C_6$)-alkylaminocarbonyl, ($C_1$–$C_6$) alkanoylamino, ($C_1$–$C_6$)-alkylsulfonylamino, ($C_5$–$C_{14}$)-arylsulfonylamino, ($C_5$–$C_{14}$)-aryl-($C_1$–$C_6$)-alkylenesulfonylamino, ($C_1$–$C_6$)-alkylaminosulfonyl, ($C_5$–$C_{14}$)-aryl-($C_{1-1}$)-alkylenaminosulfonyl, ($C_1$–$C_6$)-alkylsulfonyl, ($C_5$–$C_{14}$)-aryl-($C_1$–$C_8$)-alkylenesulfonyl or ($C_5$–$C_{14}$)-aryl-sulfonyl, said alkyl, aryl or heterocycle are optionally substituted; and wherein $R^{11}$ is hydrogen, ($C_1$–$C_{10}$)-alkyl, ($C_6$–$C_{14}$)-aryl or ($C_6$–$C_{14}$)-aryl-($C_1$–$C_6$)-alkyl, or an enantiomer, a stereoisomer, a tautomer or a mixture thereof, or a physiologically acceptable salt, a solvate or a derivative thereof, or a prodrug thereof.

2. The compound of formula (1) as defined in claim 1, wherein A is —$CH_2$—, B is —$CH_2$—CH=CH— or —$CH_2$-cyclopropyl- and $Ar^1$ is phenyl and $Ar^2$ is phenylene or a physiologically acceptable salt thereof.

3. The compound of formula (I) as defined in claim 1, having the structure (IA):

(IA)

wherein, B, X, $Ar^3$, $R^5$ and $R^1$ are as defined in claim 1 and $R^2$ and $R^3$ are the same or different and are independently selected from the group consisting of: fluorine, chlorine, bromine or a physiologically acceptable salt thereof.

4. The compound of formula (I) as defined in claim 1 wherein $R_2$ and $R_3$ are chlorine, X is CH or N and $Ar^3$ is phenyl, non-substituted or substituted by $R^8$ as defined in claim 1, or a physiologically acceptable salt thereof.

5. The compound of formula (I) as defined in claim 1, wherein $R_1$ is hydrogen, methyl or ethyl and wherein methyl or ethyl is optionally substituted by F, OH, $NH_2$, ($C_1$–$C_6$)-alkyloxy, ($C_1$–$C_6$)-alkylamino, di-($C_1$–$C_6$)-alkylamino, pyrrolidino or 2-oxo-pyrrolidino, or a physiologically acceptable salt thereof.

6. The compound of formula (I) as defined in claim 1, wherein $Ar^3$ is phenyl, non substituted or substituted by $R^8$ representing —Cl, —F, CN, —CF$_3$, —OCF$_3$, —OH, —NH$_2$, (C$_1$–C$_6$)-alkyloxy, (C$_1$–C$_6$)-alkylamino, or di-(C$_1$–C$_6$)-alkylamino or a heterocycle chosen from:

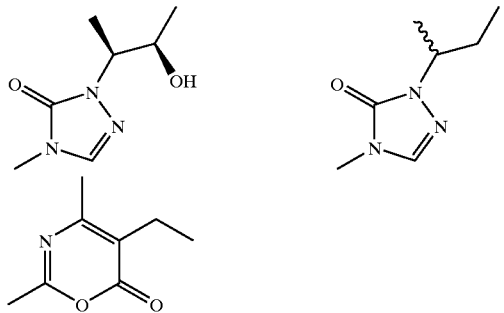

or a physiologically acceptable salt thereof.

7. The compound of formula (I) as defined in claim 1, selected from the group consisting of:
cis-4-[[2-(2,4-dichlorophenyl)-2-(1H-imidazol-1-ylmethyl)-1,3-dioxolan-4-yl]methoxy]-N-methyl-N-(3-phenyl-2(E)-propenyl)-benzenemethanamine;
4-[[2-(2,4-dichlorophenyl)-2-(1H-imidazol-1-ylmethyl)-1,3-dioxolan-4-yl]methoxy]-N-methyl-N-[3-(4-chlorophenyl-2(E)-propenyl]-1-benzenemethanamine;
cis-4-[3-[[[4-[[2-(2,4-dichlorophenyl)-2-(1H-imidazol-1-ylmethyl)-1,3-dioxan-4-yl]methoxy]phenyl]methyl]-methylamino]-1 (E)-propenyl]-phenol;
cis-4-[[2-(2,4-dichlorophenyl)-2-(1H-imidazol-1-ylmethyl)-1,3-dioxolan-4-yl]methoxy]-N-(3-phenyl-2 (E)-propenyl)-benzenemethanamine;
cis-4-[3-[[[4-[[2-(2,4-dichlorophenyl)-2-(1H-imidazol-1-ylmethyl)-1,3-dioxan yl]methoxy]phenyl]methyl]-methylamino]-1 (E)-propenyl]-phenol phosphate and trifluoroacetate;
4-[[2-(2,4-dichlorophenyl)-2-(1H-imidazol-1-ylmethyl)-1,3-dioxolan-4-yl]methoxy]-N-methyl-N-(3-phenyl-2(E)-propenyl)-1-naphthalenemethanamine;
cis-4-[[2-(2,4-dichlorophenyl)-2-(1H-imidazol-1-ylmethyl)-1,3-dioxolan-4-yl]methoxy]-N-(3-phenyl-2 (E)-propenyl)$_4$-chloro-benzenemethanamine;
cis-N-(2-aminoethyl)-4-[[2-(2,4-dichlorophenyl)-2-(1H-imidazol-1-ylmethyl)-1,3-dioxolan-4-yl]methoxy]-N-(3-phenyl-2(E)-propenyl)-benzenemethanamine trifluoroacetate;
cis-N-(2-aminoethyl)-N-[3-(4-chlorophenyl)-2(E)-propenyl]-4-[[2-(2,4-dichlorophenyl)-2-(1H-imidazol-1-ylmethyl)-1,3-dioxolan-4-yl]methoxy]-benzenemethanamine; and
cis-2-[[[4-[[2-(2,4-dichlorophenyl)-2-(1H-imidazol-1-ylmethyl)-1,3-dioxolan-4-yl]methoxy]phenyl]methyl](3-phenyl-2(E)-propenyl)amino]-ethanol.

8. A process for the preparation of a compound of formula (I) according to claim 1 comprising:
reacting a compound of formula (II):

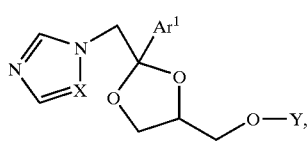

wherein Y is a leaving group and X and Ar$^1$ are as defined in claim 1, in the presence of a base, with a compound of formula (III):

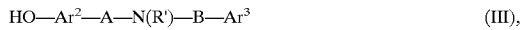

HO—Ar$^2$—A—N(R')—B—Ar$^3$ (III), wherein Ar$^2$, A, R$_1$, B and Ar$^3$ are as defined in claim 1, to obtain the corresponding compound of formula (I).

9. A process for the preparation of a compound of formula (I) according to claim 1 comprising:
reacting a compound of formula (II'):

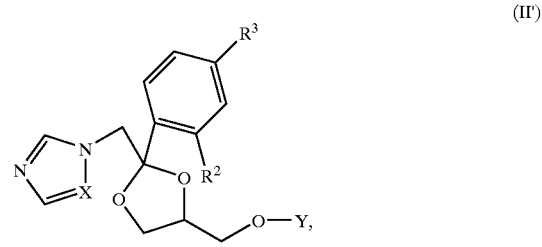

wherein Y is a leaving group and X, R$^2$ and R$^3$ are as defined in claim 1, with a compound of formula (III'):
HO—C$_6$H$_4$—CHO, (III) in the presence of a base, the phenylene of (III) is optionally substituted by R$^5$ to obtain a compound of formula (IIa):

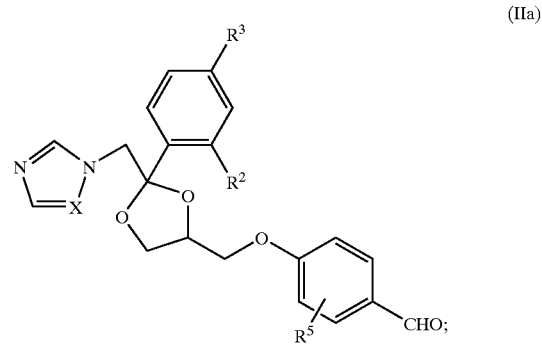

reacting compound of formula (IIa) with R$^1$—NH$_2$;
reducing the resulting product in the presence of a reducing agent such as NaBH$_3$CN, to obtain the amine of formula (IIb):

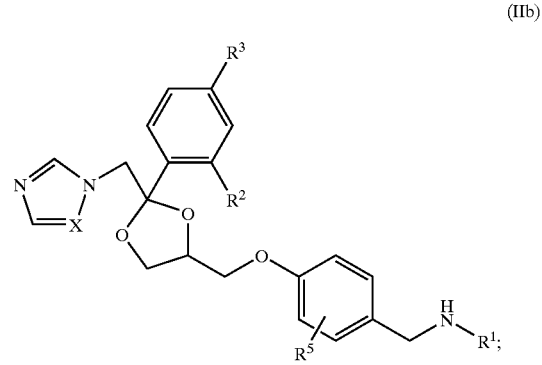

reacting the compound of formula (IIb) either with a derivative of formula:
OHC—CH=CH—C$_6$H$_4$—R$^8$ or OHC-(cyclopropyl)-C$_6$H$_4$—R$^8$ followed by a reduction reaction in the presence of a reducing agent such as NaBH$_3$CN or pyridine.BH$_3$; or reacting compound of formula (IIb) with a compound of formula:

AcO-CH$_2$—CH=CH—C$_6$H$_4$—R$^8$ in the presence of a palladium derivative to obtain the following compound of formulae (IAA) or (IAB):

(IAA)
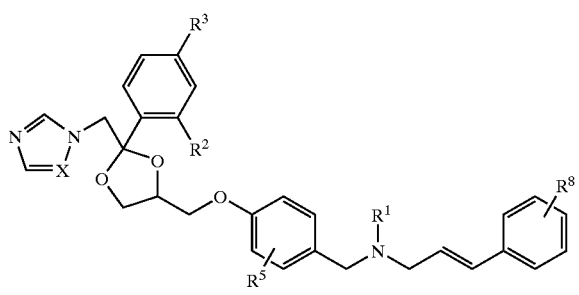

(IAB)
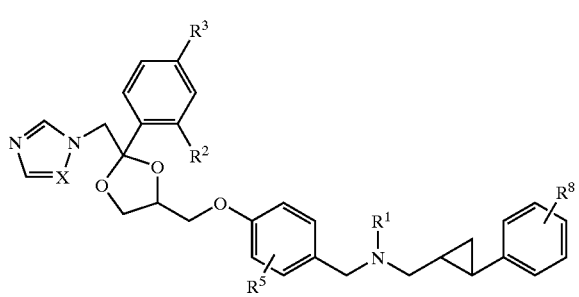

wherein X, R$^1$, R$^2$, R$^3$, R$^5$ and R$^8$ are as defined in claim 1.

10. A process for the preparation of compound of formula (I) according to claim 1 comprising:

reacting a compound of formula (IIa):

(IIa)
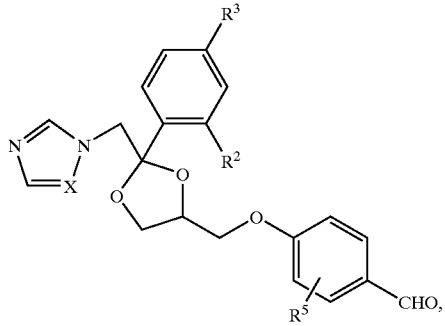

with an amine of formula R$^1$-(CH$_2$)$_2$—NH$_2$, wherein R$^1$ is F, OH, amine or a suitably protected alkylamine, pyrrolidino or 2-oxo-pyrrolidino or a dialkylamine to obtain a compound of formula (IIc) in the presence of a reducing agent such as NaBH$_3$CN;

(IIc)
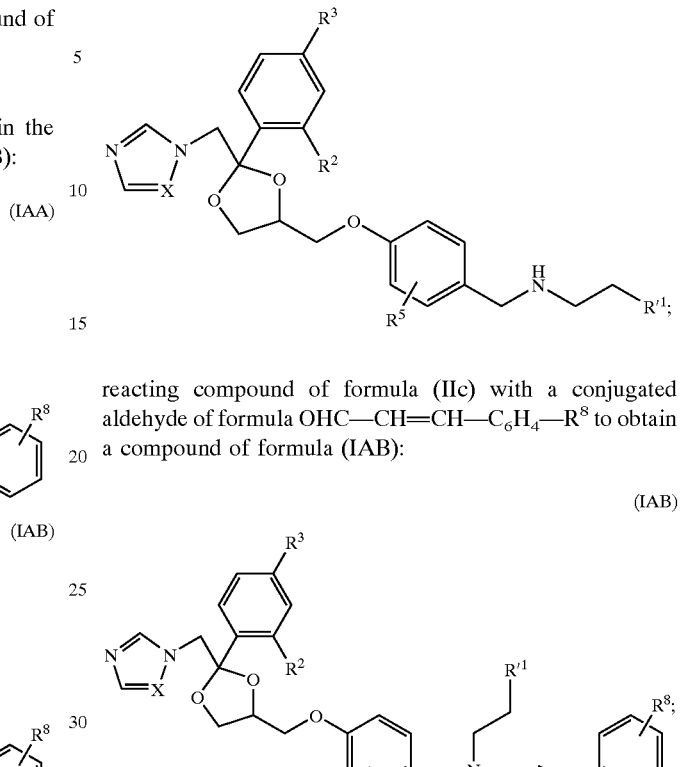

reacting compound of formula (IIc) with a conjugated aldehyde of formula OHC—CH=CH—C$_6$H$_4$—R$^8$ to obtain a compound of formula (IAB):

(IAB)
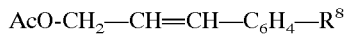

wherein X, R$^2$, R$^3$, R$^5$ and R$^8$ are as defined in claim 1.

11. A method for the treatment of a fungal disease comprising administering to a patient in need of such treatment a therapeutically effective amount of a compound of the formula (1):

(I)
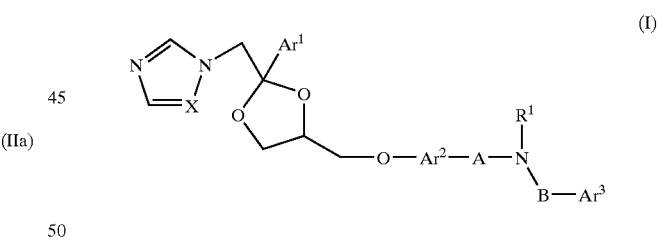

wherein

X is nitrogen or CH;

Ar$^1$ is a carbocyclic or heterocyclic aryl, non-substituted or substituted by one or more R$^2$, R$^3$ or R$^4$;

Ar$^2$ is phenylene or naphthalene, non-substituted or substituted by one or more R$^5$, R$^6$ or R$^7$;

Ar$^3$ is a carbocyclic or heterocyclic aryl, non-substituted or substituted by one or more R$^8$, R$^9$ or R$^{10}$;

A is (C$_1$–C$_4$)-alkylene or C(O);

B is (C$_1$–C$_4$)-alkylene-CH=CH— or (C$_1$–C$_4$)-alkylene-cyclopropylene, said cyclopropylene or —CH=CH— is optionally substituted by R$^2$ or R$^3$;

R$^1$ is hydrogen, —SO$_3$H or (C$_1$–C$_6$)-alkyl, non-substituted or substituted by R$^2$; and wherein R², R³, R⁴, R⁵, R⁶, R⁷, R⁸, R⁹ or R¹⁰, are the same or different and are independently selected from the group consisting of: fluorine, chlorine, bromine, cyano, mono- bi- or trihalogeno($C_1$–$C_8$)alkyl, mono- bi- or trihalogeno($C_1$–$C_8$)-alkyloxy, hydroxy, nitro, carboxyl, formyl, —SO₃H, —OSO₃H, (R¹¹O)₂P(O)—, (R¹¹O)₂P(O)—O—, amino, ($C_1$–$C_8$)-alkylamino, di(($C_1$–$C_8$)alkyl)amino, ($C_5$–$C_{14}$)-aryl-($C_1$–$C_6$)-alkylenamino or ($C_5$–$C_{14}$)-arylamino, ($C_1$–$C_8$)-alkyl, ($C_5$–$C_{14}$)-aryl, a heterocycle optionally substituted by oxo, ($C_5$–$C_{14}$)-aryl-($C_1$–$C_6$)alkyl, amino-($C_1$–$C_6$)-alkyl, ($C_1$–$C_8$)-alkylamino-($C_1$–$C_6$)-alkyl, di-(($C_1$–$C_8$)alkyl)amino-($C_1$–$C_6$)-alkyl, hydroxy-($C_1$–$C_6$)alkyl, ($C_1$–$C_6$)alkyloxy-($C_1$–$C_6$)-alkyl, ($C_1$–$C_8$)-alkyloxy optionally interrupted by one or more oxygen atoms, ($C_5$–$C_{14}$)-aryl-($C_1$–$C_6$)-alkylenoxy, ($C_5$–$C_{14}$)-aryloxy, hydroxy-($C_1$–$C_6$)alkylenoxy, ($C_1$–$C_6$)-alkyloxy-($C_1$–$C_6$)alkylenoxy, amino-($C_1$–$C_6$)alkylenoxy, ($C_1$–$C_6$)-alkylamino-($C_1$–$C_6$)-alkylenoxy, di(($C_1$–$C_8$)-alkyl)amino-($C_1$—$C_6$)-alkylenoxy, methylenedioxy, ($C_1$–$C_6$)-alkyloxycarbonyl, ($C_1$–$C_6$)-alkylcarbonyl, ($C_5$–$C_{14}$)aryl-($C_1$–$C_6$)-alkylenecarbonyl, ($C_5$–$C_{14}$)-arylcarbonyl, ($C_1$–$C_6$)-alkylaminocarbonyl, ($C_1$–$C_6$) alkanoylamino, ($C_1$–$C_6$)alkylsulfonylamino, ($C_5$–$C_{14}$) arylsulfonylamino, ($C_5$–$C_{14}$)-aryl-($C_1$–$C_6$)-alkylenesulfonylamino, ($C_1$–$C_6$)-alkylaminosulfonyl, ($C_5$–$C_{14}$)-aryl-($C_1$–$C_6$)-alkylenaminosulfonyl, ($C_1$–$C_6$)-alkylsulfonyl, ($C_5$–$C_{14}$)aryl-($C_1$–$C_8$)-alkylenesulfonyl or ($C_5$–$C_{14}$)-aryl-sulfonyl, said alkyl, aryl or heterocycle are optionally substituted; and wherein R₁ is hydrogen, ($C_1$–$C_{10}$)-alkyl, ($C_6$–$C_{14}$)-aryl or ($C_6$–$C_{14}$)-aryl-($C_1$–$C_6$)-alkyl, or an enantiomer, a stereoisomer, a tautomer or a mixture thereof, or a physiologically acceptable salt, a solvate or a derivative thereof, or a prodrug thereof, optionally in combination with a pharmaceutically acceptable carrier.

12. The method as defined in claim 11 wherein said fungal disease is caused by *Candida albicans, Candida glabrata, krusei, tropicalis, pseudotropicalis, parapsilosis, Aspergillus, Aspergillus flavus, Aspergillus niger, Cryptococcus neoformans, Microsporum canis, Trichophyton rubrun* or *Trichophyton mentagrophyte.*

13. The method as defined in claim 11 wherein said fungal disease is selected from the group consisting of candidoses, cryptococcoses, bronchopulmonary and pulmonary aspergilloses and invasive aspergilloses in immunodeficient individuals.

14. The method as defined in claim 13 wherein said candidoses is selected from the group consisting of digestive, urinary, vaginal and cutaneous candidoses.

15. The method as defined in claim 13, wherein said cryptococcoses is selected from the group consisting of neuromeningeal, pulmonary and cutaneous cryptococcoses.

16. The method as defined in claim 11, wherein said compound of formula (I) is having A is —CH₂—, B is —CH₂—CH=CH— or —CH₂-cyclopropyl- and Ar¹ is phenyl and Ar² is phenylene or a physiologically acceptable salt thereof.

17. The method as defined in claim 11, wherein said compound of formula (I) is having the structure (IA):

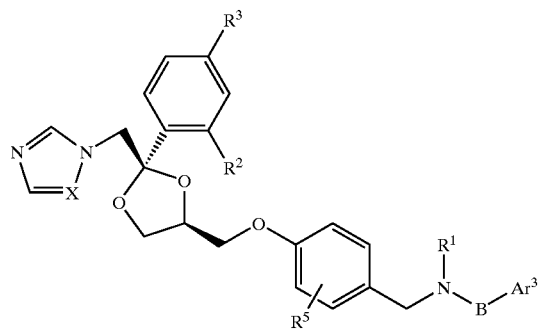

(IA)

wherein B, X, Ar³, R⁵ and R¹ are as defined in claim 11 and R² and R³ are the same or different and are independently selected from the group consisting of: fluorine, chlorine, bromine or a physiologically acceptable salt thereof.

18. The method as defined in claim 11, wherein said compound of formula (1) is having R₂ and R₃ are chlorine, X is CH or N and Ar³ is phenyl, non-substituted or substituted by R⁵ as defined in claim 11, or a physiologically acceptable salt thereof.

19. The method as defined in claim 11, wherein said compound of formula (I) is having R¹ is hydrogen, methyl or ethyl and wherein methyl or ethyl is optionally substituted by F, OH, NH 2, ($C_1$–$C_6$)-alkyloxy, ($C_1$–$C_6$)-alkylamino, di-($C_1$–$C_6$)-alkylamino, pyrrolidino or 2-oxo-pyrrolidino, or a physiologically acceptable salt thereof.

20. The method as defined in claim 11, wherein said compound of formula (I) is having Ar³ is phenyl, non substituted or substituted by R⁸ representing —Cl, —F, CN, —CF₃, —OCF₃, —OH, —NH2, ($C_1$–$C_6$)-alkyloxy, ($C_1$–$C_6$)-alkylamino, or di-($C_1$–$C_6$)alkylamino radical or a heterocycle chosen from:

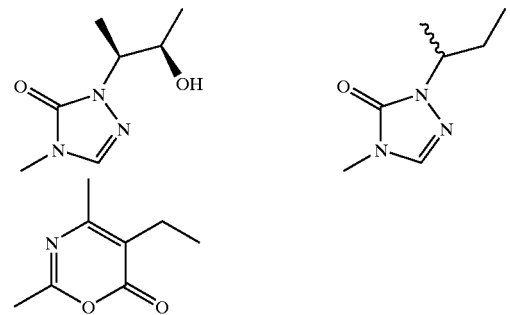

or a physiologically acceptable salt thereof.

21. The method as defined in claim 11, wherein said compound of formula (I) is selected from the group consisting of:
cis-4-[[2-(2,4-dichlorophenyl)-2-(1H-imidazol-1-ylmethyl)-1,3-dioxolan-4-yl]methoxy]-N-methyl-N-(3-phenyl-2-(E)-propenyl)-benzenemethanamine;
4-[[(2,4-dichlorophenyl)-2-(1H-imidazol-1-ylmethyl)-1,3-dioxan-4-yl]methoxy]-N-methyl-N-[3-(4-chloro-phenyl-2(E)-propenyl]-1-benzenemethanamine;
cis 4-[3-[[[4-[[2-(2,4-dichlorophenyl)-2-(1H-imidazol-1-ylmethyl)-1,3-dioxan 4-yl]methoxy]phenyl]methyl]-methylamino]-1 (E)-propenyl]-phenol;
cis-4-[[2-(2,4-dichlorophenyl)-2-(1H-imidazol-1-ylmethyl)-1,3-dioxolan-4-yl]methoxy]-N-(3-phenyl-2 (E)-propenyl)-benzenemethanamine;

cis-4-[3-[[[4-[[2-(2,4-dichlorophenyl)-2-(1H-imidazol-1-ylmethyl)-1,3-dioxan-4-yl]methoxy]phenyl]methyl]-methylamino]-1 (E)-propenyl]-phenol phosphate and trifluoroacetate;

4-[[2-(2,4-dichlorophenyl)-2-(1H 1-imidazol-1-ylmethyl)-1,3-dioxolan-4-yl]methoxy]-N-methyl-N-(3-phenyl-2 (E)-propenyl)-1-naphthalenemethanamine;

cis-4-[[2-(2,4-dichlorophenyl)-2-(1H-imidazol-1-ylmethyl)-1,3-dioxolan 4 yl]methoxy]-N-(3-phenyl-2(E)-propenyl)-4-chloro-benzenemethanamine;

cis-N-(2-aminoethyl)-4-[[2-(2,4-dichlorophenyl)-2-(1H-imidazol-1-ylmethyl)-1,3-dioxolan-4-yl]methoxy]-N-(3-phenyl-2(E)propenyl)-benzenemethanamine trifluoroacetate;

cis-N-(2-aminoethyl)-N-[3-(4-chlorophenyl)-2(E)-propenyl]4-[[2-(2,4-dichlorophenyl)-2-(1H-imidazol-1-ylmethyl)-1,3-dioxolan-4-yl]methoxy]-benzenemethanamine; and cis-2-[[[4-[[2-(2,4-dichlorophenyl)-2-(1H-imidazol-1-ylmethyl) 1,3-dioxolan-4-yl]methoxy]phenyl]methyl](3-phenyl-2(E)-propenyl)amino]-ethanol.

22. A pharmaceutical composition comprising at least one compound of formula (I) as defined in claim 1, or an enantiomer, a stereoisomer, a tautomer or a mixture thereof, or a physiologically acceptable salt, a solvate or a derivative thereof, or a prodrug thereof in combination with one or more pharmaceutically acceptable carriers.

23. A compound of formula:

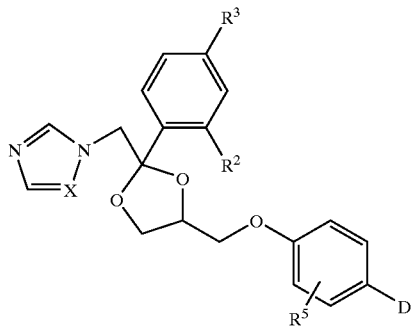

wherein

X is nitrogen or CH;

D is CHO, —$CH_2$NH—$R^1$ or —$CH_2$NH$(CH_2)_2R^1$;

$R^1$ is hydrogen, —$SO_3$H or ($C_1$–$C_6$) alkyl, non-substituted or substituted by $R^2$;

$R^1$ is F, OH, amine or a suitably protected alkylamine, pyrrolidino or 2-oxo-pyrrolidino or a dialkylamine;

$R^2$, $R^3$ or $R^5$ are the same or different and are independently selected from the group consisting of: fluorine, chlorine, bromine, cyano, mono- bi- or trihalogeno ($C_1$—C)alkyl, mono- bi- or trihalogeno($C_1$–$C_8$) alkyloxy, hydroxy, nitro, carboxyl, formyl, —$SO_3$H, —$OSO_3$H, ($R^{11}$O)$_2$P(O)—, ($R^{11}$O)$_2$P(O)O—, amino, ($C_1$–$C_8$)-alkylamino, di(($C_1$–$C_8$)alkyl)amino, ($C_5$–$C_{14}$) aryl-($C_1$–$C_6$)-alkylenamino or ($C_5$–$C_{14}$)-arylamino ($C_1$–$C_8$)-alkyl, ($C_5$–$C_{14}$)-aryl, a heterocycle optionally substituted by oxo, ($C_5$–$C_{14}$)-aryl-($C_1$–$C_6$)alkyl, amino-($C_1$–$C_6$)-alkyl, ($C_1$–$C_8$)-alkylamino-($C_1$–$C_6$)-alkyl, di-(($C_1$–$C_6$)alkyl)amino-($C_1$–$C_6$)-alkyl, hydroxy-($C_1$–$C_6$)alkyl, ($C_1$–$C_6$)-alkyloxy-($C_1$–$C_6$)-alkyl, ($C_1$–$C_8$)-alkyloxy optionally interrupted by one or more oxygen atoms, ($C_5$–$C_{14}$)-aryl-($C_1$–$C_6$)-alkylenoxy, ($C_5$–$C_{14}$)-aryloxy, hydroxy-($C_1$–$C_6$) alkylenoxy, ($C_1$–$C_6$)-alkyloxy-($C_1$–$C_6$)alkylenoxy, amino-($C_1$–$C_6$)-alkylenoxy, ($C_1$–$C_6$)-alkylamino-($C_1$–$C_6$)-alkylenoxy, di(($C_1$–$C_8$)-alkyl)amino-($C_1$–$C_6$)-alkylenoxy, methylenedioxy, ($C_1$–$C_6$)-alkyloxycarbonyl, ($C_1$–$C_6$)-alkylcarbonyl, ($C_5$–$C_{14}$) aryl-($C_1$–$C_6$)-alkylenecarbonyl, ($C_5$–$C_{14}$)-aryl-carbonyl, ($C_1$–$C_6$)-alkylaminocarbonyl, ($C_1$–$C_6$) alkanoylamino, ($C_1$–$C_6$)-alkylsulfonylamino, ($C_5$–$C_{14}$) arylsulfonylamino, ($C_5$–$C_{14}$)-aryl-($C_1$–$C_6$) alkylenesulfonylamino, ($C_1$–$C_6$)-alkylaminosulfonyl, ($C_5$–$C_{14}$)-aryl-($C_1$–$C_6$)-alkylenaminosulfonyl, ($C_1$–$C_6$)-alkylsulfonyl, ($C_5$–$C_{14}$)-aryl-($C_1$–$C_8$)-alkylenesulfonyl or ($C_5$–$C_{14}$)-arylsulfonyl, said alkyl, aryl or heterocycle are optionally substituted; and wherein $R^{11}$ is hydrogen, ($C_1$–$C_{10}$)-alkyl, ($C_6$–$C_{14}$)-aryl or ($C_6$–$C_{14}$)-aryl-($C_1$–$C_6$)-alkyl, or an enantiomer, a stereoisomer, a tautomer or a mixture thereof, or a physiologically acceptable salt, a solvate or a derivative thereof, or a prodrug thereof.

* * * * *